United States Patent
Desai et al.

(10) Patent No.: US 12,421,369 B2
(45) Date of Patent: Sep. 23, 2025

(54) POROUS POLYMER SCAFFOLDS, AND METHODS OF MAKING AND USING THE SAME

(71) Applicant: The Regents of the University of California, Oakland, CA (US)

(72) Inventors: Tejal A. Desai, San Francisco, CA (US); Ryan Chang, San Francisco, CA (US); Jasper Z. Williams, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/309,081

(22) PCT Filed: Jun. 13, 2017

(86) PCT No.: PCT/US2017/037296
§ 371 (c)(1),
(2) Date: Dec. 11, 2018

(87) PCT Pub. No.: WO2017/218565
PCT Pub. Date: Dec. 21, 2017

(65) Prior Publication Data
US 2019/0119462 A1    Apr. 25, 2019

Related U.S. Application Data

(60) Provisional application No. 62/350,003, filed on Jun. 14, 2016.

(51) Int. Cl.
| | |
|---|---|
| *C08J 9/26* | (2006.01) |
| *A61L 27/18* | (2006.01) |
| *A61L 27/24* | (2006.01) |
| *A61L 27/34* | (2006.01) |
| *A61L 27/36* | (2006.01) |
| *A61L 27/38* | (2006.01) |
| *A61L 27/54* | (2006.01) |
| *A61L 27/56* | (2006.01) |
| *B01D 39/16* | (2006.01) |

(52) U.S. Cl.
CPC ............... *C08J 9/26* (2013.01); *A61L 27/18* (2013.01); *A61L 27/24* (2013.01); *A61L 27/34* (2013.01); *A61L 27/3604* (2013.01); *A61L 27/3616* (2013.01); *A61L 27/3804* (2013.01); *A61L 27/3895* (2013.01); *A61L 27/54* (2013.01); *A61L 27/56* (2013.01); *B01D 39/1676* (2013.01); *B01D 2239/0407* (2013.01); *B01D 2239/1216* (2013.01); *C08J 2201/0446* (2013.01); *C08J 2205/044* (2013.01); *C08J 2205/048* (2013.01); *C08J 2205/05* (2013.01); *C08J 2207/10* (2013.01); *C08J 2367/04* (2013.01)

(58) Field of Classification Search
CPC .. A61L 27/56; C08J 2205/048; C08J 2207/10
See application file for complete search history.

(56) References Cited

U.S. PATENT DOCUMENTS

| | | |
|---|---|---|
| 3,755,042 A | 8/1973 | Robertson et al. |
| 4,482,053 A | 11/1984 | Alpern et al. |
| 4,750,619 A | 6/1988 | Cohen et al. |
| 5,514,378 A | 5/1996 | Mikos et al. |
| 6,103,255 A | 8/2000 | Levene et al. |
| 6,471,993 B1 | 10/2002 | Shastri et al. |
| 7,998,380 B2 | 8/2011 | Turng et al. |
| 8,097,273 B2 * | 1/2012 | Fukuhira ............... A61P 41/00 424/443 |
| 2003/0082810 A1 | 5/2003 | Serup et al. |
| 2004/0197367 A1 * | 10/2004 | Rezania ............... A61L 27/3847 424/422 |
| 2005/0268573 A1 | 12/2005 | Yan |
| 2007/0032882 A1 | 2/2007 | Lodhi et al. |
| 2009/0214614 A1 * | 8/2009 | Everland ............. A61K 38/4833 424/423 |
| 2010/0133133 A1 | 6/2010 | Hamas |
| 2011/0212179 A1 * | 9/2011 | Liu ..................... A61L 27/38 422/243 |
| 2012/0141436 A1 | 6/2012 | Bonner-Weir et al. |
| 2012/0253470 A1 * | 10/2012 | Guze .................... A61L 27/446 623/23.51 |
| 2013/0052710 A1 | 2/2013 | Ogasawara et al. |

(Continued)

FOREIGN PATENT DOCUMENTS

| | | | |
|---|---|---|---|
| ES | 2331678 | 1/2010 | |
| ES | 2331678 A1 * | 1/2010 | ............. A61L 27/46 |
| WO | WO 9425079 | 11/1994 | |

(Continued)

OTHER PUBLICATIONS dictionary.com: monolith.*
Lim et al., Nature: Scientific Reports, 2015, 11 pages.*
MErriam-Webster:plurality, 1 pg.*
Reignier et al. Polymer, 47, 13, 2006, 4703-4717.*
Merriam-Webster, "well" definition, 1 pgs.*
Kawano et al., Biomaterial Science, 2014, 2, 52-56.*
He et al., European Cells and Materials 18, 2009, 63-74.*
Crouse and Barron (2008) "Reagent Control Over the Size, Uniformity, and Composition of Co—Fe—O Nanoparticles", J. Mater. Chem. 18, 4146-4153.

(Continued)

*Primary Examiner* — Kyle A Purdy
(74) *Attorney, Agent, or Firm* — Edward J. Baba; Michael J. Blessent; Bozicevic, Field & Francis LLP

(57) ABSTRACT

Polycaprolactone (PCL) scaffolds having macropores interconnected with micorpores are provided. Tissue grafts that include the PCL scaffold having therapeutic cells encapsulated within the macropores are also provided. Also provided are methods of making the PCL scaffold and the tissue graft, and methods of transplanting cells into an individual using the tissue graft.

15 Claims, 17 Drawing Sheets

(56) References Cited

U.S. PATENT DOCUMENTS

2019/0083681 A1* 3/2019 Bhumiratana .......... A61L 27/50

FOREIGN PATENT DOCUMENTS

| WO | 2008134807 | 11/2008 |
| WO | 2009098335 | 8/2009 |

OTHER PUBLICATIONS

Raikwar et al. (2015) "Human iPS Cell-Derived Insulin Producing Cells Form Vascularized Organoids Under the Kidney Capsules of Diabetic Mice", PLoS One Journal, 28(10):1-15.

* cited by examiner

FIG. 2
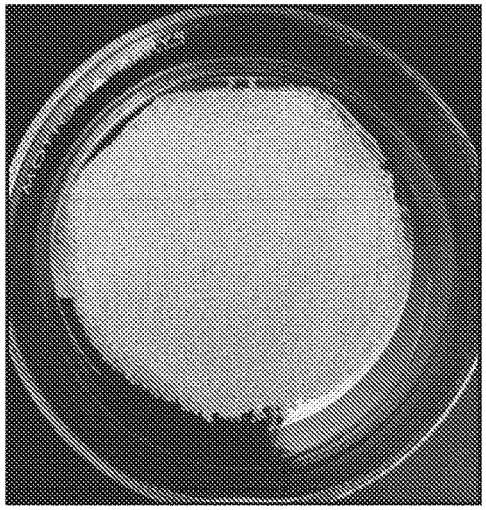
Pre-leaching
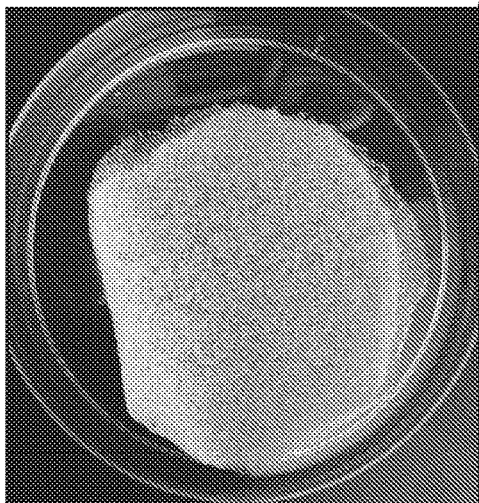
Post-leaching
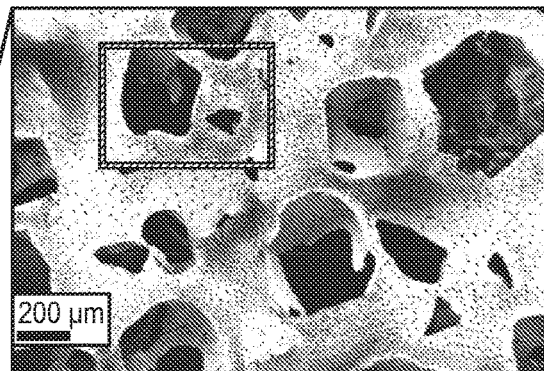
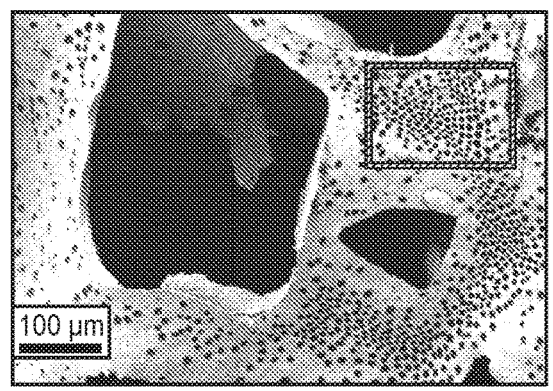
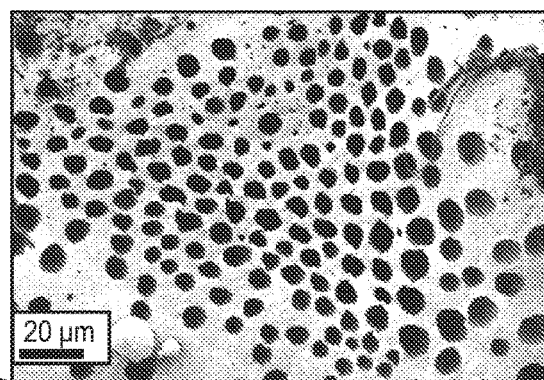

FIG. 6A
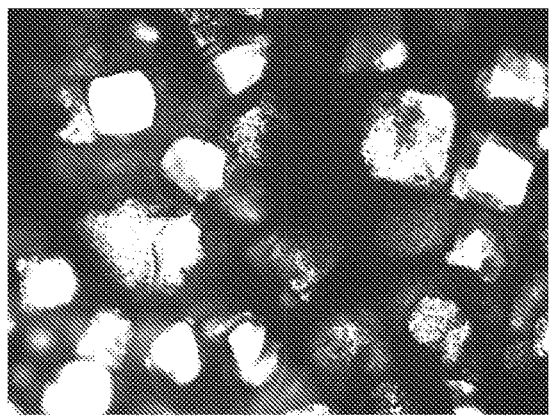
FIG. 6B
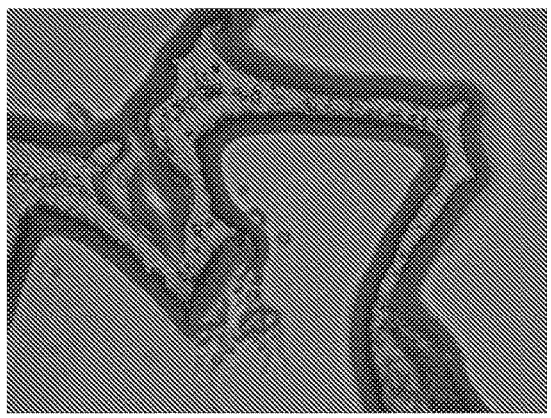
FIG. 7A
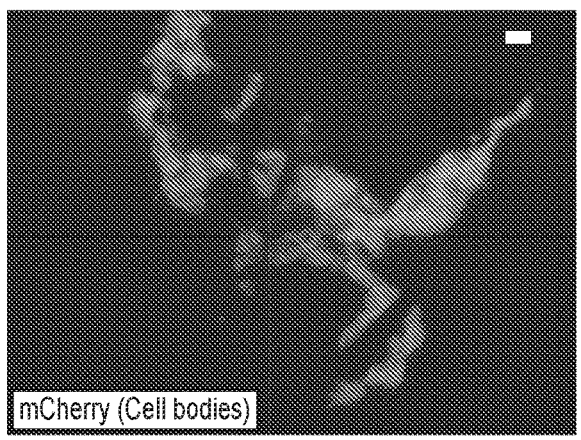
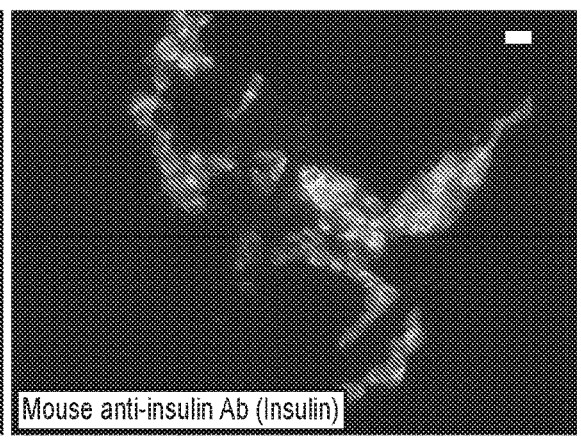
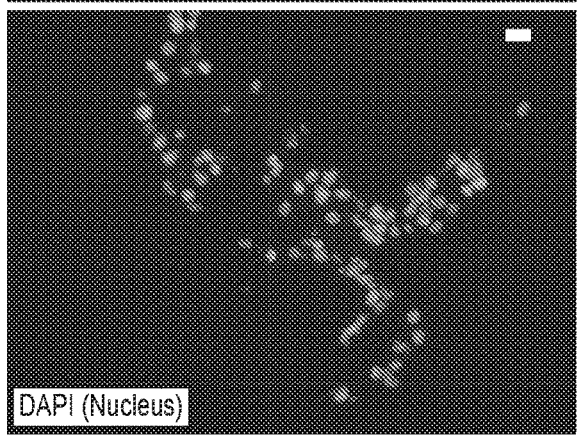

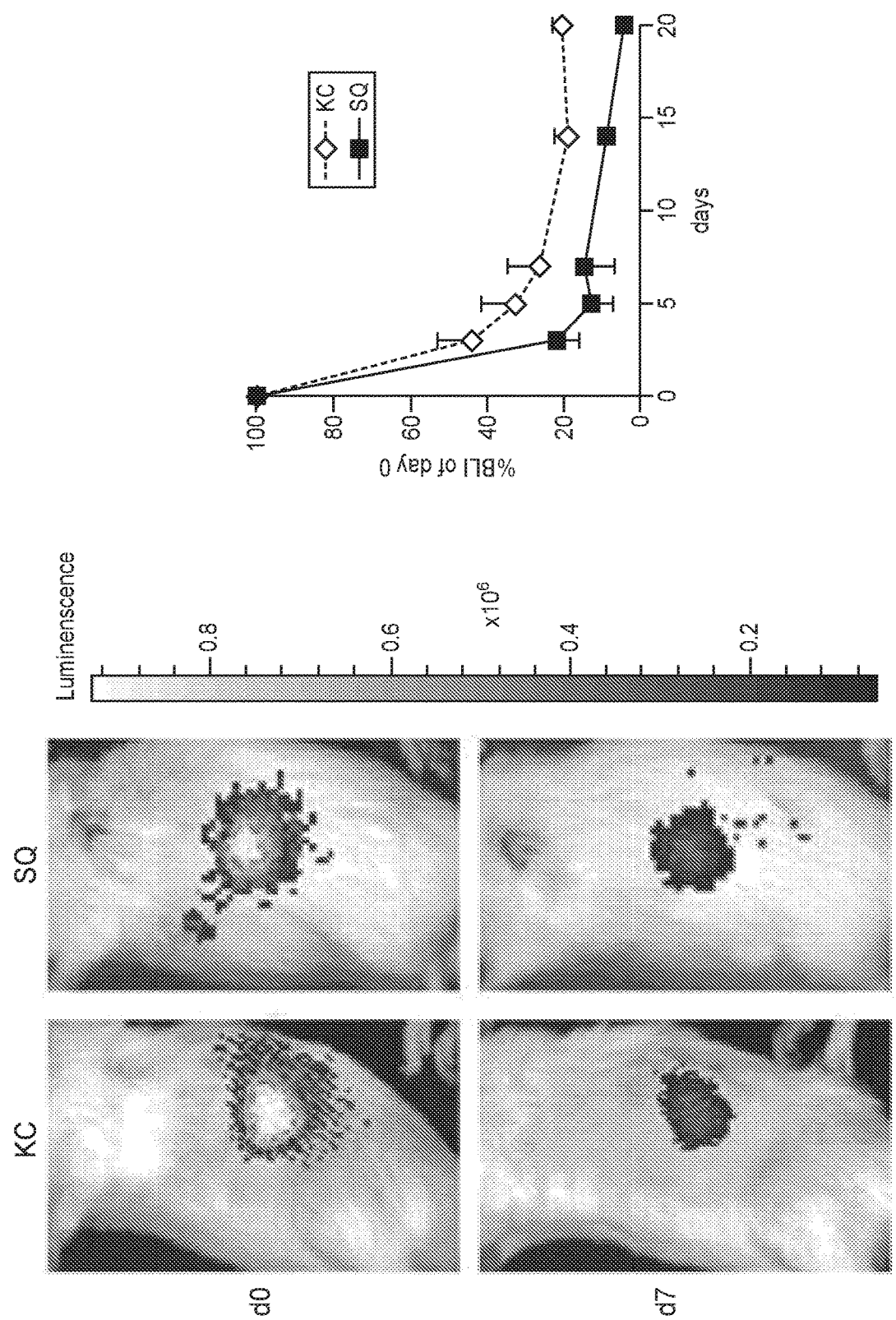

FIG. 13A
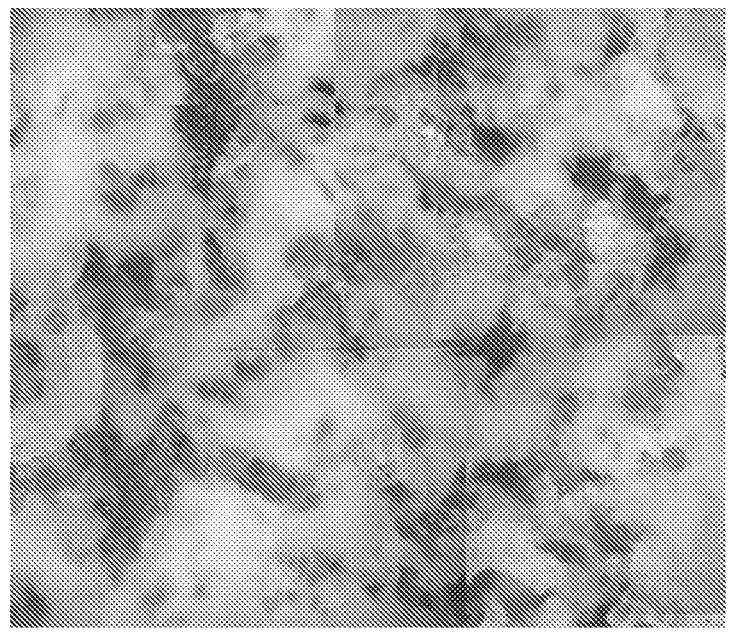
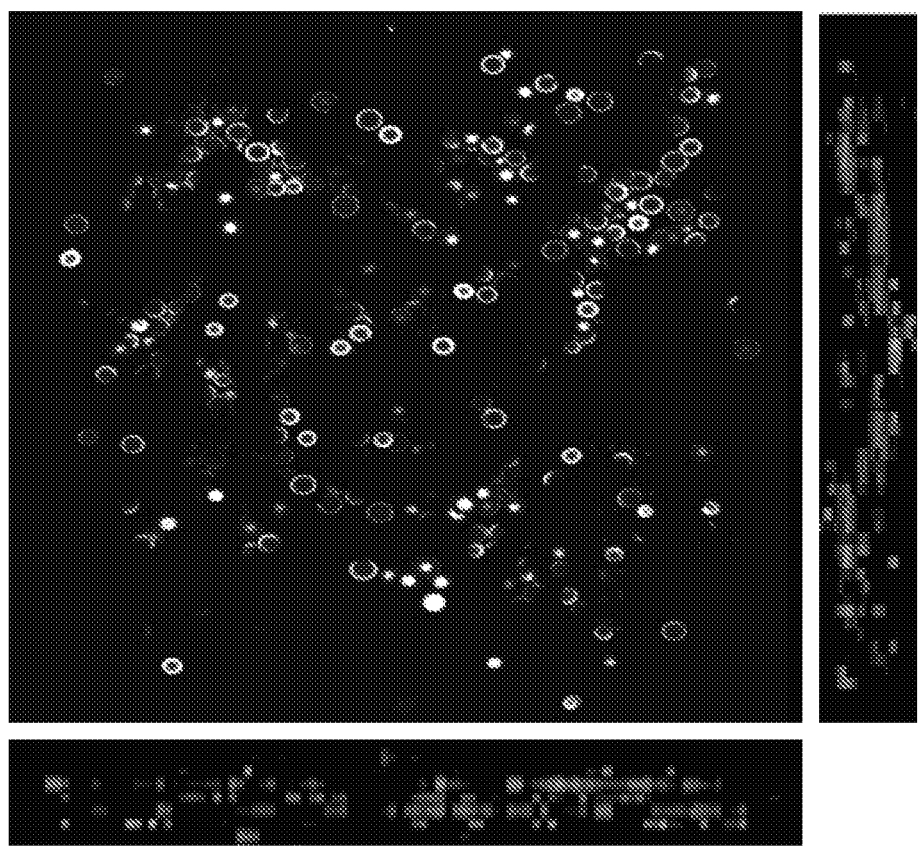

POROUS POLYMER SCAFFOLDS, AND METHODS OF MAKING AND USING THE SAME

CROSS-REFERENCE TO RELATED APPLICATIONS

This application claims the benefit of U.S. Provisional Patent Application No. 62/350,003 filed Jun. 14, 2016, which application is incorporated herein by reference in its entirety.

BACKGROUND

Cellular therapeutics provides a way to treat diseases that are not easily treated using conventional small molecule, biologics or medical device therapies. Cellular therapeutics involves transplantation of autologous, allogeneic or engineered biofunctional cells to replace, repair, and/or augment biological processes in a host organism.

SUMMARY

Polycaprolactone (PCL) scaffolds having macropores interconnected with micorpores are provided. Tissue grafts that include the PCL scaffold having therapeutic cells encapsulated within the macropores are also provided. Also provided are methods of making the PCL scaffold and the tissue graft, and methods of transplanting cells into an individual using the tissue graft.

In any embodiment, the macropores have an average diameter of from about 50 µm to about 500 µm.

In any embodiment, the micropores may have an average diameter of about 20 µm or less.

In any embodiment, the average distance between the pores may be less than about 10 µm.

In any embodiment, the PCL scaffold may have a bulk porosity of from about 50% to about 90%.

In any embodiment, the PCL scaffold may have a surface porosity of about 75% or more.

In any embodiment, the polymeric scaffold may be a subcutaneous graft scaffold.

In any embodiment, the PCL scaffold may be substantially flat. In some embodiments, the PCL scaffold has a thickness of from about 0.1 mm to about 25.0 mm. In some embodiments, the PCL scaffold has a lateral dimension of from about 1.0 cm to about 10 cm.

Also provided herein is a tissue graft containing: the polymeric scaffold according to any embodiment of the present disclosure; and a plurality of therapeutic cells encapsulated within the macropores of the PCL scaffold.

In any embodiment, the plurality of therapeutic cells may include at least $10^5$ cells.

In any embodiment, the polymeric scaffold may include a surface coating of an extracellular matrix protein. In some embodiments, the extracellular matrix protein includes collagen.

In any embodiment, the plurality of therapeutic cells may include aggregating cells. In some embodiments, the macropores have an average diameter within about 50% of an average diameter of cell aggregates formed by the aggregating cells. In some embodiments, the average diameter of the cell aggregates is from about 50 µm to about 300 µm.

In any embodiment, the therapeutic cells may include in vitro differentiated stem cells.

In any embodiment, the therapeutic cells may include insulin-secreting cells. In some embodiments, therapeutic cells include human stem cell-derived insulin producing cells (SCIPCs). In some embodiments, the SCIPCs are derived from induced pluripotent stem cells (iPS cells). In some embodiments, insulin secretion by the insulin-secreting cells is regulated by extracellular glucose.

In any embodiment, the therapeutic cells include lymphocytes. In some embodiments, the lymphocytes include T lymphocytes. In some embodiments, the T lymphocytes are tumor-specific T lymphocytes.

In any embodiment, the tissue graft may include an active agent. In some embodiments, the active agent is conjugated to a surface of the PCL scaffold. In some embodiments, the active agent is an antibody. In some embodiments, the active agent is an immunosuppressant.

Also provided is a method of transplanting cells into an individual, including implanting the tissue graft according to any embodiment of the present disclosure into an implantation site of an individual.

In any embodiment, the individual may have cancer and wherein the tissue graft comprises a therapeutically effective of the therapeutic cells to treat the cancer.

Also provided herein is a method of regulating blood glucose level in an individual, including implanting the tissue graft ding to any embodiment of the present disclosure into an implantation site of an individual, thereby maintaining normoglycemia in the individual. In some embodiments, the method includes preparing the tissue graft by culturing the insulin-secreting cells on the polymeric scaffold under conditions sufficient to encapsulate the insulin-secreting cells within the macropores of the PCL scaffold.

In any embodiment, the individual may have hyperglycemia or diabetes.

In any embodiment, the implantation site may be a subcutaneous site. In some embodiments, the implantation site is a prevascularized site. In some embodiments, the method includes vascularizing the implantation site before the implanting. In some embodiments, the vascularizing includes implanting the PCL scaffold according to any embodiment of the present disclosure at the implantation site; and removing the PCL scaffold, to vascularize of the implantation site. In some embodiments, the PCL scaffold is implanted for 90 days or less to vascularize the implantation site.

Also provided herein is a method of producing a tissue graft, including: depositing a plurality of cells on the polymeric scaffold of any one of claims 1 to 10; and culturing the deposited cells for a time period, under conditions sufficient to provide an effective amount of therapeutic cells encapsulated in the macropores of the PCL scaffold. In some embodiments, the method includes: pre-culturing an initial population of the cells, to produce a cell aggregate; loosening the cellular aggregate; and depositing the loosened cell aggregate onto the polymeric scaffold. In some embodiments, the method includes contacting the PCL scaffold with a composition containing an extracellular matrix protein before the culturing. In some embodiments, the method includes contacting the PCL scaffold with a cell culture medium before the culturing.

In any embodiment, the plurality of cells may include at least $10^4$ cells.

In any embodiment, the effective amount may include at least $10^5$ therapeutic cells.

A tissue graft made according to a method of any of the above embodiments is also provided herein.

Also provided is a method of making a polymeric scaffold, including: combining: a PCL solution containing PCL dissolved in a solvent; and a porogen, under conditions sufficient to generate a mixture containing a supersaturated solution of the porogen; depositing the mixture on a support; removing the solvent from the deposited mixture, to generate a PCL matrix; and removing the porogen from the PCL matrix, to produce a polymeric scaffold containing a plurality of pores, wherein the plurality of pores includes macropores interconnected by micropores.

In any embodiment, the solvent may include 2,2,2-trifluoroethanol, chloroform, dimethyl oxalate (DMO), ethylene carbonate (EC), N-methyl acetamide (NMA), dimethyl sulfoxide (DMSO), acetic acid (AA), 1,4-dioxane (DO), dimethyl carbonate (DMC), dichloromethane (DCM), naphthalene, sulfalene, trimethylurea, ethylene glycol and related glycols or polyglycols, N-methyl pyrrolidone (NMP), ethylene carbonate, hexane, and/or ethanol.

In any embodiment, the PCL solution may have a concentration of from about 10 mg/ml to about 500 mg/ml.

In any embodiment, the support may be a silicon wafer.

In any embodiment, removing the solvent may include evaporating the solvent.

In any embodiment, the porogen may be water soluble. In some embodiments, the porogen is an alkali metal salt. In some embodiments, the porogen is sodium chloride or potassium chloride. In some embodiments, removing the porogen includes submerging the PCL matrix in an aqueous solution. In some embodiments, the aqueous solution is distilled water.

A polymeric scaffold made according to a method of any of the above embodiments is also provided herein.

Kits that include the present polymeric scaffolds or the present tissue grafts are also provided.

BRIEF DESCRIPTION OF THE FIGURES

The skilled artisan will understand that the drawings, described below, are for illustration purposes only. The drawings are not intended to limit the scope of the present teachings in any way.

FIG. 2 is a collection of images showing a porous PCL scaffold at different stages of fabrication and different magnifications, according to embodiments of the present disclosure. The length of each scale bar is as indicated.

FIGS. 6A and 6B are a collection of images showing gross morphology and cellular attachment, respectively, of MIN6 cells cultured on a porous PCL scaffold, according to embodiments of the present disclosure.

FIGS. 7A and 7B are a collection of fluorescent and bright field images, respectively, showing staining for the indicated structures in MIN6 cells cultured on porous PCL scaffold, according to embodiments of the present disclosure. The scale bar is 10 µm.

FIGS. 10A-10E are a collection of images showing distribution of therapeutic cells in a tissue graft, according to embodiments of the present disclosure.

FIGS. 13A-13C show characterization of loading efficiency and capacity of PCL scaffolds, according to embodiments of the present disclosure.

DEFINITIONS

Figure 1:
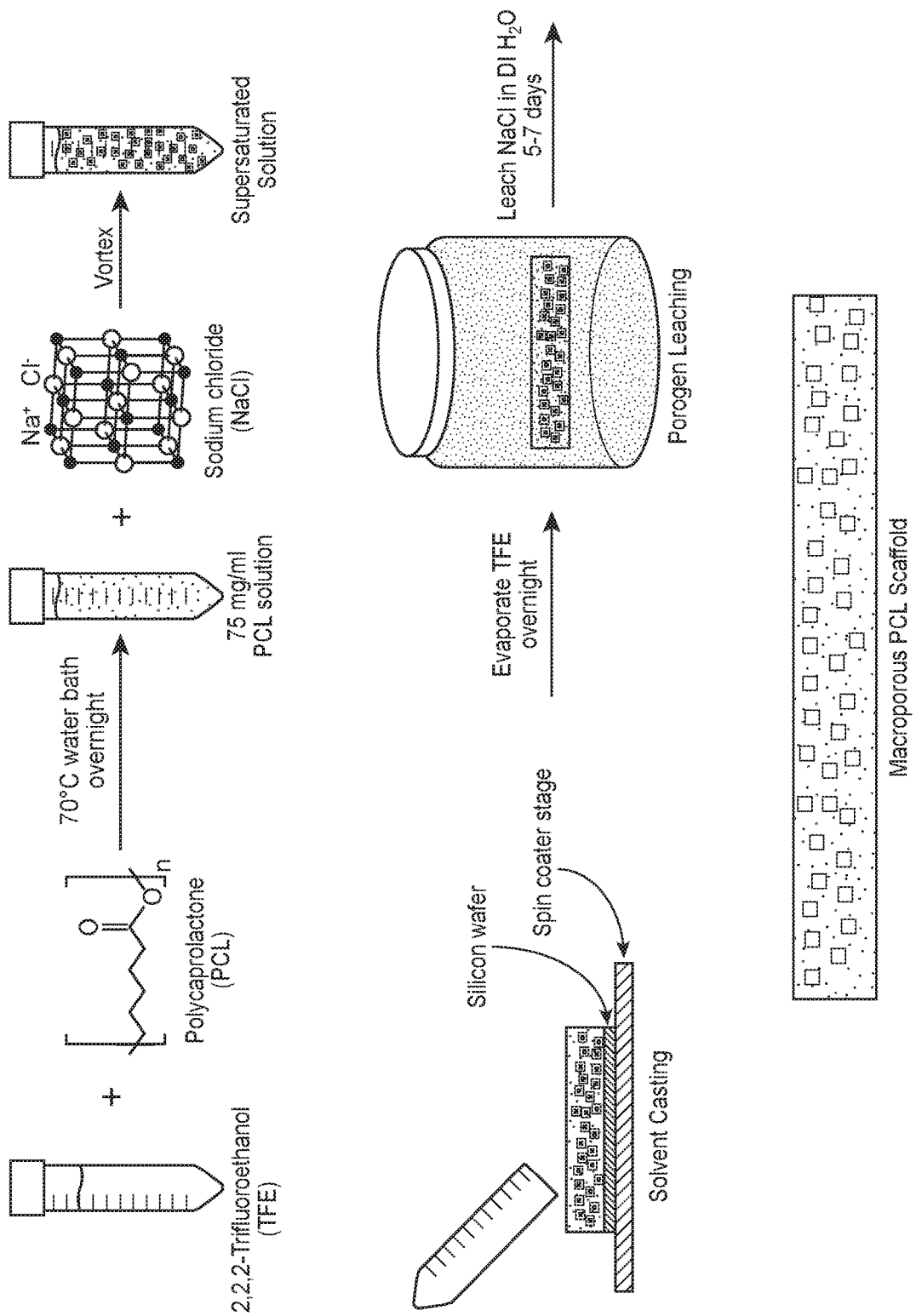
FIG. 1 is a schematic diagram depicting a method of fabricating a porous PCL scaffold, according to embodiments of the present disclosure.

The term "about" as used herein when referring to a measurable value, such as a physical quantity and the like, is meant to encompass variations of ±20%, such as ±10%, such as ±5%, ±1%, including ±0.1% from the specified value, as such variations are typical of measurements characterizing the disclosed subject matter or appropriate to perform the disclosed methods.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

The term "about" as used herein when referring to a measurable value such as an amount, a length, and the like, is meant to encompass variations of ±20% or ±10%, more preferably ±5%, even more preferably ±1%, and still more preferably ±0.1% from the specified value, as such variations are typical of measurements characterizing the disclosed structures, or appropriate to perform the disclosed methods.

An "individual" as used herein, refers to an animal, such as a mammal, including a human or a non-human mammal, non-human primate (e.g., chimpanzee), monkey, canine (e.g., dog), feline (e.g., cat), murine (e.g., mouse, rat), ungulate (e.g., cow, pig, sheep, camel, horse), etc.

As used herein, the terms "treat," "treatment," "treating," and the like, refer to obtaining a desired surgical and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Polymeric" as used herein, may be used to describe an organic compound composed of repeating units of one or more monomers containing carbon and hydrogen atoms.

The monomers can also include other atoms such as Si, O, N, P, and S. A polymer may have a solid bulk polymer matrix.

"Biocompatible," as used herein, refers to a property of a material that allows for prolonged contact with a tissue in a subject without causing toxicity or significant damage.

"Active agent" and "drug" are used interchangeably to refer to any chemical compound that can have a therapeutic and/or preventive effect for a disease when suitably administered to a subject.

"Therapeutically effective amount" refers to an amount effective, at dosages and for periods of time necessary, to achieve the desired therapeutic result.

As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type.

Stem cells include pluripotent stem cells, which can form cells of any of the body's tissue lineages: mesoderm, endoderm and ectoderm. Therefore, for example, stem cells can be selected from a human embryonic stem (ES) cell; a human inner cell mass (ICM)/epiblast cell; a human primitive ectoderm cell, a human primitive endoderm cell; a human primitive mesoderm cell; and a human primordial germ (EG) cell. Stem cells also include multipotent stem cells, which can form multiple cell lineages that constitute an entire tissue or tissues, such as but not limited to hematopoietic stem cells or neural precursor cells. Stem cells also include totipotent stem cells, which can form an entire organism. In some embodiments, the stem cell is a partially differentiated or differentiating cell. In some embodiments, the stem cell is an induced pluripotent stem cell (iPSC), which has been reprogrammed or de-differentiated.

"Substantially" as used herein, may be applied to modify any quantitative representation that could permissibly vary without resulting in a change in the basic function to which it is related. For example, a scaffold may have dimensions that deviate somewhat from being flat, if the cell encapsulation and/or tissue graft properties of the scaffold is not materially altered.

"Diameter" as used in reference to a shaped structure (e.g., macropore, micropore, cell aggregate, etc.) refers to a length that is representative of the overall size of the structure. The length may in general be approximated by the diameter of a circle of sphere that circumscribes the structure.

"Flat" as used herein, refers to a shape of an object having wide lateral dimensions compared to a smaller height or depth. The object may have a top surface and bottom surface, each defined by edges extending along the lateral dimensions. The top and bottom surfaces may be substantially parallel to each other.

"Host" as used in reference to an implant, tissue graft or cell transplant, is meant to refer to the individual or tissue that receives the implant, tissue graft or cell transplant.

"Normoglycemia" as used herein, refers to having an actual or measured level of glucose in the blood that is within the range of glucose level of a healthy individual (i.e., a range of glucose level that in the long-term does not cause detrimental effects on the health of the individual). The level of glucose may fluctuate based on the feeding status of the individual.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Certain ranges are presented herein with numerical values being preceded by the term "about." The term "about" is used herein to provide literal support for the exact number that it precedes, as well as a number that is near to or approximately the number that the term precedes.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

DETAILED DESCRIPTION

As summarized above, a polymeric scaffold made of polycaprolactone (PCL) and that contains macropores interconnected with micropores is provided. The present polymeric scaffold may provide an environment, e.g., microenvironment, for various types of cells, such as differentiated or differentiating stem cells, to attach and grow therein. The polymeric scaffold having cells encapsulated therein may then provide a carrier for transplanting the cells into a physiological site, by implanting the polymeric scaffold at the site. Also provided herein is a tissue graft that includes the present polymeric scaffold and therapeutic cells encapsulated within the macropores of the PCL scaffold. In some cases, where the cells grow as aggregates (where two or more cells are attached to one another) when grown in a conventional culture environment (e.g., grown on a two-dimensional culture dish or flask surface), the macropores have an average diameter that approximates the average size of the cell aggregates.

The polymeric scaffold and tissue graft of the present disclosure may have one or more desirable properties. In some cases, the polymeric scaffold may provide for maintenance or growth of the cells cultured therein for a time period (e.g., one day or more, two days or more, 3 days or more, 4 days or more, 5 days or more, 6 days or more, 8 days or more, 10 days or more including 15 days or more) in in vitro culture. Thus, cells encapsulated in the present polymeric scaffold may at least maintain the same number of cells, or may expand by two times or more, e.g., 3 times or more, 4 times or more, 5 times or more, 10 times or more, 20 times or more 50 times or more, including 100 times or more in number after the time period in culture as compared to before (i.e., when the cells are initially seeded on the scaffold). In some cases, cells encapsulated in the present polymeric scaffold expands by a range of 2 to 1000 fold, e.g., 2 to 100 fold, 2 to 50 fold, including 3 to 20 fold in number after the time period in culture as compared to before.

The polymeric scaffold, with or without cells encapsulated therein, may promote vascularization when the scaffold is implanted into a physiological site (e.g., subcutaneous site) of an individual. The implantation site may be vascularized in 60 days or less, e.g., 40 days or less, 30 days or less, 20 days or less, 10 days or less, including 5 days or less after implantation of the polymeric scaffold, with or without cells encapsulated therein. In some cases, the implantation site is vascularized in 5 days to 60 days, e.g., 5 days to 40 days, including 10 days to 30 days after implantation of the polymeric scaffold, with or without cells encapsulated therein. In some cases, the vascularization occurs with little or no fibrosis around the scaffold, at the interface between the host tissue and the scaffold.

A tissue graft of the present disclosure containing therapeutic cells may maintain the cells in a functional state suitable for providing a therapeutic effect (e.g., insulin secretion by beta-cells; cytolytic activity by T cells; etc.) when implanted into a physiological site (e.g., subcutaneous site, tumor, etc.) of an individual. The therapeutic cells may maintain responsiveness to physiological cues (e.g., blood glucose level, antigen-presenting cell, etc.) at the implantation site.

Without wishing to be held to theory, it is thought that the porosity (i.e., the macro- and micro-porosity) of the polymeric scaffold presents to the encapsulated cells a microenvironment that provides desirable nutrient transport and vascular integration to grow and maintain the cells in a functional state.

Further aspects of the present disclosure are now described.

Polymeric Scaffolds

A polymeric scaffold of the present disclosure includes a polycaprolactone (PCL) scaffold. The PCL scaffold may contain macropores and micropores generally throughout the scaffold structure (FIG. 2, FIG. 9D). The macropores may be present within the scaffold, and may be present on the external surface (i.e., the surface facing the exterior) of the scaffold. The micropores may be present within the scaffold, and may be present on the external surface of the scaffold. The PCL scaffold may be a solid-cast structure, a foam, woven or knitted structure, or may be a non-woven structure. In some embodiments, the PCL scaffold is a monolithic, continuous structure that includes pores (e.g., macropores and micropores). As shown in FIG. 2, the present polymeric scaffold may be characterized by a network of struts that define the macropores, where the struts contain micropores that form interconnections between the macropores.

The position of each macropore and micropore in a scaffold may be unpatterned. In other words, the position of macropores and micropores between distinct scaffolds having the same shape and size may vary, and the spatial distribution of the macropores and micropores may not be substantially identical between the distinct scaffolds.

The macropores generally have an average diameter of about 50 μm or more, e.g., about 60 μm or more, about 70 μm or more, about 80 μm or more, about 90 μm or more, including about 100 μm or more, and may have an average diameter of about 500 μm or less, e.g., about 400 μm or less, about 300 μm or less, about 250 μm or less, including about 200 μm or less. In some embodiments, the macropores have an average diameter in the range of about 50 μm to about 500 μm, e.g., about 60 μm to about 400 μm, about 70 μm to about 300 μm, about 80 μm to about 250 μm, including about 90 μm to about 200 μm.

The micropores generally have an average diameter of about 0.1 μm or more, e.g., about 0.5 μm or more, about 1.0 μm or more, about 2.0 μm or more, about 3.0 μm or more, including about 5.0 μm or more, and may have an average diameter of about 20 μm or less, e.g., about 18 μm or less, about 16 μm or less, about 14 μm or less, about 12 μm or less, including about 10 μm or less. In some embodiments, the micropores have an average diameter in the range of about 0.1 μm to about 20 μm, e.g., about 0.5 μm to about 18 μm, about 1.0 μm to about 16 μm, about 2.0 μm to about 14 μm, including about 3.0 μm to about 12 μm.

The average distance between neighboring pores (e.g., average of the shortest distance from an edge of a micropore or a macropore, to an edge of neighboring pore, whether it is a macropore or a micropore) may vary, and may be about 0.1 μm or more, e.g., about 0.5 μm or more, about 1.0 μm or more, including about 2.0 μm or more, and in some cases, may be about 20 μm or less, e.g., about 10 μm or less, about 5.0 μm or less, about 2.0 μm or less, including about 1.0 μm or less. In some embodiments, the average distance between neighboring pores is in the range of about 0.1 μm to about 20 μm, e.g., about 0.5 μm to about 10 μm, including about 1.0 μm to about 10 μm.

The present polymeric scaffold may have a suitable bulk porosity for supporting growth and/or maintenance of cells encapsulated therein. In some cases, the scaffold has a bulk porosity of about 50% or more, e.g., about 55% or more, about 60% or more, about 65% or more, about 70% or more, including about 75% or more, and in some cases, has a bulk porosity of about 95% or less, e.g., about 90% or less, about 85% or less, about 80% or less, including about 75% or less. In some embodiments, the scaffold has a bulk porosity in the range of about 50% to about 95%, e.g., about 55% to about 90%, about 60% to about 85%, including about 65% to about 80%. In some cases, the scaffold has a bulk porosity of about 75%. The bulk porosity may be measured using computed tomography (CT) scanning to create a 3D rendering.

The present polymeric scaffold may have a suitable surface porosity for supporting growth and/or maintenance of cells encapsulated therein. In some cases, the scaffold has a surface porosity of about 75% or more, e.g., about 80% or more, about 85% or more, about 90% or more, about 95% or more, including about 97% or more, and in some cases, has a surface porosity of about 99% or less, e.g., about 98% or less, about 97% or less, about 96% or less, including about 95% or less. In some embodiments, the scaffold has a surface porosity in the range of about 75% to about 99%, e.g., about 80% to about 99%, about 85% to about 98%, including about 90% to about 98%. The surface porosity may be measured by segmentation of an image of the surface of the scaffold to determine the area of the material versus the area of the pores visible in microscope images, using, e.g., a visual segmentation software.

The present polymeric scaffold may have any suitable ratio of macropores to micropores per unit volume of the scaffold, for supporting growth and/or maintenance of cells encapsulated therein. In some embodiments, the scaffold has a ratio of macropores to micropores of on average about 1:50 or less, e.g., about 1:100 or less, about 1:200 or less, about 1:300 or less, about 1:400 or less, about 1:500 or less, about 1:600 or less, about 1:700 or less, about 1:800 or less, about 1:900 or less, about 1:1,000 or less, including about 1:5,000 or less per unit volume of the scaffold, and in some cases a ratio of on average about 1:10,000 or more, e.g., about 1:5,000 or more, about 1:1,000 or more, about 1:900 or more, about 1:800 or more, about 1:700 or more, about 1:600 or more, about 1:500 or more, about 1:400 or more, about 1:300 or more, about 1:200 or more, including about 1:100 or more per unit volume of the scaffold. In some embodiments, the scaffold has a ratio of macropores to micropores of, on average, from about 1:10,000 to about 1:5,000, from about 1:5,000 to about 1:1,000, from about 1:1,000 to about 1:900, from about 1:900 to about 1:800, from about 1:800 to about 1:700, from about 1:700 to about 1:600, from about 1:600 to about 1:500, from about 1:500 to about 1:400, from about 1:400 to about 1:300, from about 1:300 to about 1:200, from about 1:200 to about 1:100, including about 1:100 to about 1:50 per unit volume of the scaffold.

The present polymeric scaffold is structurally designed to degrade under physiological conditions (e.g., in vivo in an implantation site) over a predetermined duration, such as for example 0.5 days or longer, such as 1 day or longer, such as 2 days or longer, such as 5 days or longer, such as 7 days or longer, such as 10 days or longer, such as 14 days or longer, such as 21 days or longer, such as 28 days or longer, such as 70 days or longer, such as 100 days or longer, such as 200 days or longer, such as 300 days or longer, such as 600 days or longer, and including 1,000 days or longer. In other embodiments, a polymeric scaffold of interest are configured to degrade when exposed to physiological conditions at a predetermined rate, such as at a substantially zero-order degradation rate, such as at a substantially first order degradation rate and including at a substantially second-order degradation rate. The degradation rate may depend on various structural factors of the scaffold, including the density of the PCL polymer forming the scaffold and the porosity (e.g., the macroporosity and/or the microporosity) of the scaffold, etc.

The stiffness of the scaffold may vary and may depend on the density of the PCL polymer forming the scaffold and the porosity (e.g., the macroporosity and/or the microporosity) of the scaffold, etc. In some cases, the scaffold is pliable and may readily bend under constant stress (see FIG. 9B). In some embodiments, the Young's modulus (E) of the scaffold is about 0.1 mega pascals (MPa) or more, e.g., about 0.5 MPa or more, about 1.0 MPa or more, about 5.0 MPa or more, about 10 MPa or more, including about 50 MPa or more, and in some cases, is about 100 MPa or less, e.g., about 50 MPa or less, about 10 MPa or less, about 5.0 MPa or less, about 1.0 MPa or less, including about 0.5 MPa or less. In some embodiments, the Young's modulus (E) of the scaffold is from about 0.1 MPa to about 0.5 MPa, from about 0.5 MPa to about 1.0 MPa, from about 1.0 MPa to about 5.0 MPa, from about 5.0 MPa to about 10 MPa, from about 10 MPa to about 50 MPa, or from about 50 MPa to about 100 MPa. The Young's modulus of the scaffold may be measured using, e.g., a three-point bending test.

The present polymeric scaffold may have any suitable three-dimensional form for implanting at a physiological site in an individual. In some cases, the polymeric scaffold has a form factor that is suitable for implanting at a subcutaneous site. In some cases, the polymeric scaffold is substantially flat. The thickness of a substantially flat scaffold may vary, and may be about 0.1 millimeters (mm) or more, e.g., about 0.2 mm or more, about 0.3 mm or more, about 0.5 mm or more, about 0.75 mm or more, about 1.0 mm or more, including about 2.0 mm or more, and in some cases may be about 25 mm or less, e.g., about 20 mm or less, about 15 mm or less, about 10 mm or less, about 8.0 mm or less, about 6.0 mm or less, about 5.0 mm or less, about 4.5 mm or less, about 4.0 mm or less, about 3.5 mm or less, about 3.0 mm or less, about 2.5 mm or less, including about 2.0 mm or less. In some cases, the substantially flat scaffold has a thickness in the range of about 0.1 mm to about 25 mm, e.g., about 0.2 mm to about 20 mm, about 0.2 to about 10 mm, about 0.2 to about 6.0 mm, about 0.3 mm to about 4.0 mm, about 0.5 mm to about 3.5 mm, including about 1.0 mm to about 3.0 mm.

The present polymeric scaffold may have one or more surfaces with any suitable shape. For example, a substantially flat polymeric scaffold may have a top and bottom surfaces that are in a suitable shape. In some cases, the shape of the surface is circular, square, rectangular, oval, triangular, hexagonal, octagonal, pentagonal, diamond-shaped, parallelogram-shaped, etc. In some cases, the polymeric scaffold is substantially disc-shaped, having a circular face (see, FIG. 9A).

The present polymeric scaffold may have any suitable lateral dimensions (e.g., width and/or length, or diameter). In some cases, the polymeric scaffold has a lateral dimension of about 1.0 centimeter (cm) or more, e.g., about 2.0 cm or more, about 3.0 cm or more, about 4.0 cm or more, including 5 cm or more, and in some cases has a lateral dimension of about 10 cm or less, e.g., about 9.0 cm or less, about 8.0 cm or less, about 7.0 cm or less, about 6.0 cm or less, including about 5.0 cm or less. In some embodiments, the polymeric scaffold has a lateral dimension in the range of about 1.0 cm to about 10 cm, e.g., about 1.0 cm to about 9.0 cm, about 2.0 cm to about 8.0 cm, including about 3.0 cm to about 7.0 cm.

Tissue Grafts

Also provided herein is a tissue graft that includes a polymeric PCL scaffold, as described above, and therapeutic cells encapsulated within the macropores of the PCL scaffold. The therapeutic cells are, in some cases, stably encapsulated within the scaffold such that the cells remain in the scaffold when the tissue graft is implanted at an implantation site, e.g., a subcutaneous site, of an individual. In some cases, about 20% or less, e.g., about 15% or less, about 10% or less, about 5% or less, about 2% or less, about 1% or less, about 0.1% or less, about 0.01% or less, including about 0.001% or less of the total number of therapeutic cells encapsulated in the scaffold may exit the scaffold when implanted at an implantation site of an individual. In some cases, the therapeutic cells can migrate out of the scaffold when the tissue graft is implanted at an implantation site of an individual. The extent to and/or rate at which therapeutic cells exit the scaffold when the tissue graft is implanted at an implantation site of an individual may be vary, and may depend on a variety of controllable factors, such as the size of the pores (macropores and/or micropores), the size of the pores (macropores and/or micropores) relative to the size of the cells or cell aggregates encapsulated in the scaffold, the degradation rate of the PCL polymer, the density of the PCL polymer, the porosity of the scaffold, surface modification of the scaffold, etc.

The present tissue graft may have encapsulated therein any suitable amount of the therapeutic cells. The amount of cells may depend on a variety of factors, such as the function provided by the therapeutic cells, the size of the tissue graft, the length of time the tissue graft is to be implanted, the condition to be treated by the tissue graft and/or the desired therapeutic outcome. In some cases, the tissue graft includes at least $10^5$ cells, e.g., at least $10^6$ cells, at least $10^7$ cells, at least $10^8$ cells, at least $10^9$ cells, at least $10^{10}$ cells, or more cells.

In some embodiments, the therapeutic cells are aggregating cells. Aggregating cells may be cells that, when grown on the surface of a culture dish or in suspension, attach to one another to form clumps (i.e., aggregates) of two or more cells, e.g., 10 or more cells, 100 or more cells, 1,000 or more cells, including 10,000 or more cells. The aggregate of cells may also be attached to a solid support (e.g., the culture dish surface) or may be free-floating in the medium. The aggregate of cells may be any suitable shape, and in some cases, may be spherical or oval.

The size of the aggregate may be any suitable size. In some cases, the cell aggregate that forms in a conventional culture condition (e.g., in suspension, or on a two-dimensional surface) has an average diameter that approximates the average diameter of the macropores of the present polymeric scaffold. Thus, in some cases, the therapeutic cells may form, in a conventional culture condition, cell aggregates having an average diameter that is within about 50%, e.g., within about 40%, within about 30%, within about 20%, within about 10%, including within about 5% of the average diameter of the macropores of the polymeric scaffold of the present tissue graft. In some embodiments, the therapeutic cells may form, in a conventional culture condition, cell aggregates having an average diameter of about 50 µm or more, e.g., about 75 µm or more, about 100 µm or more, including about 125 µm or more, and in some cases, an average diameter of about 300 µm or less, e.g., about 275 µm or less, about 250 µm or less, about 225 µm or less, including about 200 µm or less. In some cases, the therapeutic cells may form, in a conventional culture condition, cell aggregates having an average diameter in the range of about 50 µm to about 300 µm, e.g., about 75 µm to about 275 µm, about 75 µm to about 250 µm, about 100 µm to about 225 µm, including about 100 µm to about 200 µm.

The aggregate of cells may be a collection of a substantially pure population of cells, or may be a collection of a plurality of types, e.g., two more types, three or more types, four or more types, including 5 or more types, of cells. In some cases the aggregate of cells is stem cell-derived. In some cases, the aggregate of cells is an embryoid body that includes pluripotent stem cells and/or cells differentiated therefrom.

In some cases, the therapeutic cells include cells that secrete a biological agent, e.g., a signaling molecule, a hormone, a growth factor, an enzyme, an antibody, etc. In some cases, the therapeutic cells include cells (e.g., immune cells, such as cytotoxic T lymphocytes) that interact with targets at or in the vicinity in the host tissue in which the tissue graft is implanted. In some cases, the therapeutic cells include cells whose activity is conditional, e.g., cells that modulate their function based on the physiological state of the host, such as glucose level in the blood and/or the environment of the host tissue. The therapeutic cell may be a type of cell that specifically possesses the functional activity by virtue of its cell type (e.g., by differentiating or having differentiated into a cell type that exhibits the functional activity), or may be genetically modified to exhibit the functional activity that was not exhibited by the cell before being genetically modified. Suitable methods for genetically modification are described in, e.g., US 20130052710, which is incorporate herein by reference.

In some cases, the therapeutic cells encapsulated in the polymeric scaffold secretes a therapeutic molecule, e.g., hormone, cytokine, enzyme, antibody, etc. Suitable therapeutic molecules that can be secreted include, without limitation, insulin, human growth hormone, thyroxin GLP-1, GLP-1 (7-37), and like GLP-1 receptor agonist polypeptides, GLP-2, interleukins 1 to 33 (e.g., IL-1, IL-2, IL-3, IL-4, IL-5, IL-6, IL-7, IL-8, IL-9, IL-10, IL-11, IL-12, IL-13, IL-17, IL-18, IL-21, IL-22, IL-27, IL-33), interferon ($\alpha$, $\beta$, $\gamma$), GM-CSF, G-CSF, M-CSF, SCF, FAS ligands, TRAIL, leptin, adiponectin, blood coagulation factor VIII/ blood coagulation factor IX, von Willebrand factor, glucocerebrosidase, lipoprotein lipase (LPL), lecithin-cholesterol acyltransferase (LCAT), erythropoietin, apoA-I, albumin, atrial natriuretic peptide (ANP), luteinizing hormone releasing hormone (LHRH), angiostatin/endostatin, endogenous opioid peptides (enkephalins, endorphins, etc.), calcitonin/ bone morphogenetic protein (BMP), pancreatic secretory trypsin inhibitors, catalase, superoxide dismutase, anti-TNF-$\alpha$ antibody, soluble IL-6 receptor, IL-1 receptor antagonist, $\alpha 2$ antitrypsin, etc.

The therapeutic cells may be any suitable type of cell for transplanting to an individual in need. The cells may be autologous, allogeneic, xenogeneic or genetically-modified.

In some cases, the therapeutic cells are stem cell-derived cells. Stem cells of interest include, without limitation, hematopoietic stem cells, embryonic stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, hematopoietic stem cells, induced pluripotent stem cells; and the like; as well as differentiated cells that can be cultured in vitro and used in a therapeutic regimen, where such cells include, but are not limited to, keratinocytes, adipocytes, cardiomyocytes, neurons, osteoblasts, pancreatic islet cells, retinal cells, and the like. The cell that is used will depend in part on the nature of the disorder or condition to be treated.

Suitable human embryonic stem (ES) cells include, but are not limited to, any of a variety of available human ES lines, e.g., BG01 (hESBGN-01), BG02 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UC01 (HSF-1), UC06 (HSF-6) (University of California, San Francisco; San Francisco, Calif.); WA01 (H1), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIH) code, followed in parentheses by the provider code.

Hematopoietic stem cells (HSCs) are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

Mesenchymal stem cells (MSC), originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC.

An induced pluripotent stem (iPS) cells is a pluripotent stem cell induced from a somatic cell, e.g., a differentiated somatic cell. iPS cells are capable of self-renewal and differentiation into cell fate-committed stem cells, including neural stem cells, as well as various types of mature cells.

iPS cells can be generated from somatic cells, including skin fibroblasts, using, e.g., known methods. iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and K1f4. In some embodiments, somatic cells are genetically modified with one or more expression constructs comprising nucleotide sequences encoding Oct-4, Sox2, Nanog, and LIN28. Methods of generating iPS are known in the art, and any such method can be used to generate iPS.

In some cases, the therapeutic cells are lymphocytes, such as CD4+ and/or CD8+ T lymphocytes, or B lymphocytes. In some embodiments, the therapeutic cells are cytotoxic T lymphocytes. In some embodiments, the lymphocytes are genetically modified lymphocytes, e.g., chimeric antigen receptor (CAR) T lymphocytes. The lymphocytes, e.g., cytotoxic T lymphocytes, may specifically recognize an antigen that is associated with a disease, e.g., cancer or tumor, that is to be treated in the tissue graft host.

In some embodiments, the therapeutic cells include insulin-secreting cells. The insulin-secreting cells may be any suitable type of insulin-secreting cell. In some cases, the insulin-secreting cells are a type of cell that secretes insulin (e.g., pancreatic β islet cells, or β-like cells).

In some cases, the insulin-secreting cells are primary β islet cells (e.g., mature β islet cells isolated from a pancreas). In some cases, the insulin-secreting cells are β cells, or β-like cells that are derived in vitro from immature cell, precursor cells, progenitor cells, or stem cells. The insulin-secreting cells may be derived from (i.e., obtained by differentiating) stem and/or progenitor cells such as hepatocytes (e.g., transdifferentiated hepatocytes), acinar cells, pancreatic duct cells, stem cells, embryonic stem cells (ES), partially differentiated stem cells, non-pluripotent stem cells, pluripotent stem cells, induced pluripotent stem cells (iPS cells), etc. Suitable insulin-secreting cells and methods of generating the same are described in, e.g., US20030082810; US20120141436; and Raikwar et al. (PLoS One. 2015 Jan. 28; 10(1):e0116582), each of which are incorporated herein by reference.

The insulin-secreting cells may produce, e.g., secrete, insulin at a rate independently of the ambient/extracellular glucose concentration (e.g., the concentration of glucose in the host tissue in which the tissue graft is implanted), or may produce, e.g., secrete, insulin at a rate that depends on the ambient/extracellular glucose concentration. In some cases, the insulin-secreting cells constitutively secrete insulin. In some embodiments, the insulin-secreting cells increase insulin secretion when the ambient/extracellular glucose concentration increases, and decreases insulin secretion when the ambient/extracellular glucose concentration decreases.

The present tissue graft may include a suitable coating on the PCL scaffold (e.g., on the surface of the macropores and/or micropores of the scaffold) to promote encapsulation of the therapeutic cells. The coating may include a biological coating (e.g., extracellular matrix proteins) and/or may include a synthetic coating (such as described in US20070032882, which is incorporated herein by reference). A suitable biological coating includes extracellular matrix proteins, such as, without limitation, collagen, fibronectin, vitronectin, laminin, heparan sulfate, proteoglycan, glycosaminoglycan, chondroitin sulfate, hyaluronan, dermatan sulfate, keratin sulfate, elastin, and combinations thereof. In some embodiments, the polymeric scaffold is coated with collagen, type I.

In some embodiments, the present tissue graft includes one or more active agents adsorbed or absorbed within the polymer scaffold and where the polymer scaffold is configured to deliver the one or more active agents to a site of implantation. In some embodiments, the active agent is an immunosuppressant, such as, but not limited to cyclosporine and tacrolimus.

In some cases, the active agent is an inhibitor of mammalian target of rapamycin (mTOR), such as, without limitation, rapamycin and analogs thereof (e.g., sirolimus, temsirolimus, everolimus, deforolimus, etc.). The mTOR inhibitor may be used as an immunosuppressant, or may be an anticancer agent.

In some cases, the active agent is a binding agent, such as an antibody, or an antigen binding fragment thereof. The antibody may be any suitable antibody that specifically binds to an antigen expressed by a therapeutic cell of interest for encapsulating in the present scaffolds. Suitable antigens include, without limitation, CD3, CD28, CD137, CTLA-4, TNF, IL-6, IL-12, PD-1, PD-L1, TIM3, LAG3, IL-2Ralpha, IL-23, IL-6R, CD25, IL-17, IL-1, CD4, CD8, LFA-1, IL-22, and IL-20.

Other suitable active agents according to embodiments of the present disclosure may include but are not limited to interferon, interleukin, erythropoietin, granulocyte-colony stimulating factor (GCSF), stem cell factor (SCI:), leptin (OB protein), interferon (alpha, beta, gamma), antibiotics such as vancomycin, gentamicin ciprofloxacin, amoxycillin, *lactobacillus*, cefotaxime, levofloxacin, cefipime, mebendazole, ampicillin, *lactobacillus*, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-IO, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of active agents.

In some embodiments, the one or more absorbed active agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDFS, GDF6, GDF8, recombinant human growth factors, cartilage-derived morphogenetic proteins (CDMP), CDMP-1, CDMP-2 and CDMP-3. In certain instances, the present polymeric scaffold includes bone morphogenetic protein 2 (BMP-2).

Methods

Methods of Making a Polymeric Scaffold and/or a Tissue Graft

Also provided herein is a method of making a polymeric scaffold and/or the tissue graft of the present disclosure. A method of making a polymeric scaffold, as described herein, may be described with reference to FIG. 1. In general terms, the present method may include combining a solution of polycaprolactone (PCL) in a solvent with a porogen, to generate a mixture containing a supersaturated solution of the porogen. A "porogen" as used herein may refer to any material that can be incorporated into a matrix to reserve a space in the matrix, and can be removed from the matrix to generate a pore. The mixture may be deposited on a solid support, e.g., a silicon wafer, a mold, etc., and the solvent may be removed (e.g., by evaporation) from the deposited mixture, to form a PCL matrix that is shaped according to the manner in which the mixture spread within the confines provided by the solid support. The porogen then may be removed from the PCL matrix using any suitable method, depending on the porogen, to produce the porous (e.g., microporous and macroporous) PCL scaffold.

The PCL solution may be any suitable solution. In some cases, the solvent is an organic solvent. In some cases, the solvent is a volatile organic solvent. Suitable solvents include, without limitation, 2,2,2-trifluoroethanol (TFE), chloroform, dimethyl oxalate (DMO), ethylene carbonate (EC), N-methyl acetamide (NMA), dimethyl sulfoxide (DMSO), acetic acid (AA), 1,4-dioxane (DO), dimethyl carbonate (DMC), dichloromethane (DCM), naphthalene, sulfalene, trimethylurea, ethylene glycol and related glycols or polyglycols, N-methyl pyrrolidone (NMP), ethylene carbonate, hexane, ethanol, and combinations thereof.

The PCL solution may have any suitable concentration of PCL. In some cases, the PCL solution contains PCL at about 10 mg/ml or more, e.g., about 25 mg/ml or more, about 50 mg/ml or more, including about 70 mg/ml or more, and in some cases contains PCL at about 500 mg/ml or less, e.g., about 200 mg/ml or less, about 100 mg/ml or less, including about 80 mg/ml or less. In some embodiments, the PCL solution contains PCL at a range of about 10 mg/ml to about 500 mg/ml, e.g., about 25 mg/ml to about 200 mg/ml, including about 50 mg/ml to about 100 mg/ml.

The PCL solution may be prepared using any suitable method. In some cases, the PCL solution is prepared by combining a starting PCL material with the solvent to produce a mixture, and incubating the mixture under sufficient conditions (e.g., at an elevated temperature) to generate the PCL solution. The starting PCL material may have the general unit structure:

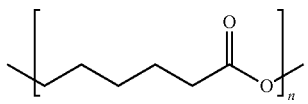

where n is an integer greater than 2, e.g., 10 or more, 100 or more, $10^3$ or more, $10^4$ or more, including $10^5$ or more. The PCL may have any suitable molecular weight. In some cases, the number average molecular weight ($M_n$) of the PCL is 5,000 Dalton (Da) or more, e.g., 10,000 Da or more, 15,000 Da or more, 20,000 Da or more, 30,000 Da or more, 40,000 Da or more, 50,000 Da or more, 75,000 Da or more, including 100,000 Da or more, and in some cases the $M_w$ is 1,000,000 Da or less, e.g., 750,000 Da or less, 500,000 Da or less, 250,000 Da or less, 200,000 Da or less, 150,000 Da or less, including 100,000 Da or less. In some embodiments, the $M_w$ of the PCL is in the range of 5,000 Da to 1,000,000 Da, e.g., 10,000 Da to 750,000 Da, 10,000 Da to 500,000 Da, 15,000 Da to 250,000 Da, 20,000 Da to 200,000 Da, including 20,000 Da to 150,000 Da. The Mn may be as measured by Gel Permeation Chromatography with refractive index detection relative to polystyrene standards.

In some cases, the mixture of the starting PCL material and solvent is incubated at an elevated temperature (e.g., at a range of 50° C. to 90° C., e.g., 60° C. to 80° C., including 65° C. to 75° C.) for a sufficient period of time (e.g., 1 hour (hr) or longer, 2 hr or longer, 3 hr or longer, 4 hr or longer, 6 hr or longer, 8 hr or longer, 10 hr or longer, including 12 hr or longer).

The porogen may be any suitable material (e.g., chemical substance) that can be incorporated into the PCL matrix to reserve a space, and be removed from the scaffold to form pores in the PCL matrix. In some embodiments, the porogen is water soluble. Water soluble porogens of interest include water soluble salts, such as an alkali metal salt, an alkali earth metal salt, ammonium salt; sugars, polysaccharides; and water soluble synthetic or natural polymers. In some cases, the water-soluble salt is a chloride salt. In some cases, the alkali metal salt is sodium chloride or potassium chloride. In some embodiments, the porogen is a heat-labile compound, such as sodium bicarbonate or hydrogen peroxide.

The porogen may be a particulate material, where the particles of the porogen remain suspended in the mixture of PCL solution and porogen. The particulate porogen may have any suitable particle size, where the particle size may depend on the desired size of the macropores in the PCL scaffold. The porogen particle size may be similar to the size of the macropores. In some embodiments, the porogen particles have an average diameter of about 50 μm or more, e.g., about 60 μm or more, about 70 μm or more, about 80 μm or more, about 90 μm or more, including about 100 μm or more, and may have an average diameter of about 500 μm or less, e.g., about 400 μm or less, about 300 μm or less, about 250 μm or less, including about 200 μm or less. In some embodiments, the porogen particles have an average diameter in the range of about 50 μm to about 500 μm, e.g., about 60 μm to about 400 about 70 μm to about 300 about 80 μm to about 250 including about 90 μm to about 200 μm.

The amount of porogen added to form the mixture of PCL solution and porogen may be any suitable amount, and may depend on the desired density of macropores in the PCL scaffold. In some embodiments, the amount of particulate porogen (e.g., NaCl) added is about $10^4$ particles/g PCL in solution or more, e.g., about $3 \times 10^4$ particles/g PCL in solution or more, about $6 \times 10^4$ particles/g PCL in solution or more, about $10^5$ particles/g PCL in solution or more, about $3 \times 10^5$ particles/g PCL in solution or more, including about $6 \times 10^5$ particles/g PCL in solution or more, and in some embodiments, is about $10^9$ particles/g PCL in solution or less, e.g., about $6 \times 10^8$ particles/g PCL in solution or less, $3 \times 10^8$ particles/g PCL in solution or less, about $10^8$ particles/g PCL in solution or less, about $6 \times 10^7$ particles/g PCL in solution or less, about $3 \times 10^7$ particles/g PCL in solution or less, about $10^7$ particles/g PCL in solution or less, about $6 \times 10^6$ particles/g PCL in solution or less, including about $3 \times 10^6$ particles/g PCL in solution or less. In some embodiments, the amount of particulate porogen (e.g., NaCl) added is from about $10^4$ particles/g PCL in solution to about $10^9$ particles/g PCL in solution, e.g., from about $3 \times 10^4$ particles/g PCL in solution to about $6 \times 10^8$ particles/g PCL in solution, from about $6 \times 10^4$ particles/g PCL in solution to about $3 \times 10^8$ particles/g PCL in solution, from about $10^5$ particles/g PCL in solution to about $10^8$ particles/g PCL in solution, from about $10^5$ particles/g PCL in solution to about $6 \times 10^7$ particles/g PCL in solution, from about $10^5$ particles/g PCL in solution to about $3 \times 10^7$ particles/g PCL in solution, including from about $10^5$ particles/g PCL in solution to about $10^7$ particles/g PCL in solution.

In some embodiments, the amount of NaCl added as porogen to the PCL solution is about 0.1 g/g PCL in solution or more, e.g., 0.5 g/g PCL in solution or more, 1.0 g/g PCL in solution or more, 2.0 g/g PCL in solution or more, 3.0 g/g PCL in solution or more, including 4.0 g/g PCL in solution or more, and in some cases, is about 50 g/g PCL in solution or less, e.g., 40 g/g PCL in solution or less, 30 g/g PCL in solution or less, 20 g/g PCL in solution or less, including 10 g/g PCL in solution or less. In some embodiments, the amount of NaCl added as porogen to the PCL solution is from about 0.1 g/g PCL in solution to about 50 g/g PCL in solution, e.g., from about 0.5 g/g PCL in solution to about 40 g/g PCL in solution, from about 1.0 g/g PCL in solution to about 30 g/g PCL in solution, from about 2.0 g/g PCL in solution to about 20 g/g PCL in solution, from about 3.0 g/g PCL in solution to about 20 g/g PCL in solution, including from about 4.0 g/g PCL in solution to about 10 g/g PCL in solution.

The mixture of the PCL solution and porogen may be deposited on the solid support using any suitable method, which may depend on the type of solid support. In some cases, the solid support is a level surface, such as a surface of a silicon wafer. Where the solid support is a level surface, the mixture may be deposited onto the surface to form a film on the surface. In some embodiments, the level surface may be spun (e.g., using a spin coater stage) to create a film of the mixture having a substantially even thickness across the film. In some embodiments, the solid support is a mold or cast.

Removing the solvent may be done using any suitable method. In some cases, removing the solvent includes evaporating the solvent. In some cases, evaporating the solvent includes exposing the deposited mixture to a vacuum, heat, convective flow of a gas (e.g., air, nitrogen, argon, etc.) or a combination thereof. In some cases, the solvent is evaporated by lyophilizing the deposited mixture. Removing the solvent may be done for a sufficient period of time (e.g., 1 hr or longer, 2 hr or longer, 3 hr or longer, 4 hr or longer, 6 hr or longer, 8 hr or longer, 10 hr or longer, including 12 hr or longer) to remove 90% or more, e.g., 95% or more, 97% or more, 99% or more, or substantially all the solvent from the mixture.

The porogen may be removed from the PCL matrix using any suitable method, depending on the porogen used. In some cases, removing the porogen includes submerging the PCL matrix in an aqueous solution (e.g., distilled water) to leach out the porogen, e.g., when the porogen is a water-soluble salt. In some cases, removing the porogen includes exposing the PCL matrix to heat, where the porogen is heat labile. Removing the porogen may be done for a sufficient period of time (e.g., 1 hr or longer, 3 hr or longer, 6 hr or longer, 12 hr or longer, 1 day or longer, 3 days or longer, 5 days or longer, including 7 days or longer), and the length of time may depend on the porogen and the method of removal. After the removal step, 80% or more, e.g., 85% or more, 90% or more, 95% or more, 97% or more, or substantially all the porogen may be removed from the PCL matrix.

As discussed herein, a polymeric scaffold of the present disclosure may be used as a component of a tissue graft by having therapeutic cells encapsulated in the macropores of the scaffold. Thus, provided herein is a method of making a tissue graft that includes a porous (e.g., microporous and macroporous) PCL scaffold and therapeutic cells encapsulated in the macropores of the PCL scaffold. The present method may be described with reference to FIG. 3. In general terms, the method may include depositing cells of interest on the present polymeric scaffold, and culturing in vitro the deposited cells for a sufficient time under suitable conditions to maintain, expand and/or differentiate the cells, thereby providing an effective amount of therapeutic cells encapsulated in the macropores of the PCL scaffold.

In some embodiments, where the cells are aggregating cells, as described above, the method may include pre-culturing a first population of the cells in conventional culture conditions (e.g., on a two dimensional culture dish surface, or in suspension), to produce a cell aggregate, loosening the cell aggregate, and depositing the loosened cell aggregate onto the polymeric scaffold.

The number of cells that encapsulated in the scaffold after the culturing in the present method may be at least as much as the number of cells that are initially deposited on the scaffold. In some embodiments, the present method expands the number of cells initially deposited on the scaffold by about 1.2 fold or more, e.g., about 1.5 fold or more, about 2.0 fold or more, about 3.0 fold or more, about 5.0 fold or more, about 10 fold or more, about 20 fold or more, about 30 fold or more, about 50 fold or more, about 100 fold or more, about 200 fold or more, about 500 fold or more, about 1,000 fold or more, including about 10,000 fold or more to produce the encapsulated cells. In some embodiments, the present method expands the number of cells initially deposited on the scaffold by a range of about 1.2 fold to about 1.5 fold, about 1.5 fold to about 2.0 fold, about 2.0 fold to about 3.0 fold, about 3.0 fold to about 5.0 fold, about 5.0 fold to about 10 fold, about 10 fold to about 20 fold, about 20 fold to about 30 fold, about 30 fold to about 50 fold, about 50 fold to about 100 fold, about 100 fold to about 200 fold, about 200 fold to about 500 fold, about 500 fold to about 1,000 fold, or about 1,000 fold to about 10,000 fold.

The number of cells deposited on the polymeric scaffold may be any suitable number. In some cases, the number of cells deposited on the polymeric scaffold is $10^4$ cells or more, e.g., $10^5$ cells or more, $10^6$ cells or more, including $10^7$ cells or more, and in some cases, may be $10^{12}$ cells or less, e.g., $10^{11}$ cells or less, $10^{10}$ cells or less, $10^9$ cells or less, $10^8$ cells or less, $10^7$ cells or less, including $10^6$ cells or less. In some embodiments, the number of cells deposited on the polymeric scaffold is in the range of $10^4$ cells to $10^{12}$ cells, e.g., $10^4$ cells to $10^{10}$ cells, $10^4$ cells to $10^8$ cells, including $10^4$ cells to $10^7$ cell.

The cells deposited on the scaffold may be any suitable type of cells (e.g., therapeutic cells and/or precursors thereof, as described above). In some cases, the cells deposited on the scaffold are fully differentiated, therapeutic cells (e.g., primary cells, in vitro differentiated stem cells or precursor cells, etc.). In some cases, the cells deposited on the scaffold are undifferentiated stem cells, partially differentiated cells and/or precursor cells, and the cells may start or continue to differentiate while being cultured in the scaffold.

In some cases, the present method includes precoating the PCL scaffold before depositing the cells. The scaffold may be precoated with a suitable coating material to facilitate attachment of the cells to the scaffold. The coating material may be any suitable biological of synthetic coating material, as described above. The PCL scaffold may be coated with the coating material using any suitable method (e.g., by contacting the scaffold with a solution that contains an appropriate amount of the coating material, under suitable conditions). In some cases, the PCL scaffold, with or without the coating material, is conditioned with the culture medium before depositing the cells (e.g., by contacting the PCL scaffold, with or without the coating material, with the culture medium, under suitable conditions (such as at 37° C. for 6-18 hr).

Methods of Transplanting Cells into an Individual

Also provided herein is a method of transplanting cells into an individual, using a tissue graft made of a porous (e.g., macroporous and microporous) PCL scaffold, as described herein, e.g., to treat a disease. The method may include implanting (e.g., surgically implanting) a tissue graft that contains a porous (e.g., microporous and macroporous) polymeric scaffold and therapeutic cells encapsulated in the pores (e.g., macropores) of the PCL scaffold, as described herein, into an implantation site of a host individual. The host may be suffering from a condition, e.g., a disease, that may be treated by providing the therapeutic cells to the individual. In some cases, the disease is diabetes (type 1 or type 2). In some cases, the individual has pre-diabetes, or hyperglycemia. In some cases, the disease is cancer (e.g., breast cancer, prostate cancer, brain cancer, skin cancer, lung cancer, liver cancer, colorectal cancer, etc.). The therapeutic cells may be any suitable therapeutic cells, as described above, and the type of therapeutic cells may depend on the disease to be treated.

The implantation site may be any suitable location (e.g., surgically accessible location) in the individual. In some cases, the implantation site is a subcutaneous site. In some cases, the implantation site is at or in the vicinity of a tissue that is affected by the disease (e.g., a tissue with a solid tumor).

In some cases, the implantation site is a prevascularized site, where the implantation site is not sufficiently vascularized to support the therapeutic cells before being vascularized. Thus, in some embodiments, the present method includes vascularizing the implantation site before implanting the tissue graft. The implantation site may be vascularized using any suitable method. In some embodiments, the implantation site is vascularized by using a porous (e.g., macroporous and microporous) PCL scaffold, as described herein. Thus, in some embodiments, the present method includes implanting a cell-free porous (e.g., macroporous and microporous) PCL scaffold (i.e. the PCL scaffold with no cells encapsulated therein), as described above, at the implantation site for time period sufficient to vascularize the implantation site, and then removing the PCL scaffold. Then, the tissue graft loaded with the therapeutic cells, as described herein, may be implanted at the vascularized implantation site.

In some cases, the vascularization of the implantation site may be done by a cell-free porous (e.g., macroporous and microporous) scaffold that is made of a biocompatible polymer other than PCL, such as polypropylene. Thus, in some cases, the cell-free porous (e.g., macroporous and microporous) scaffold is a polypropylene scaffold.

The cell-free porous (e.g., macroporous and microporous) PCL scaffold may be implanted at the implantation site for a suitable period of time sufficient to vascularize the implantation site. The period of time may be 90 days or less, e.g., 60 days or less, 45 days or less, 30 days or less, including 20 days or less. In some cases, the period of time sufficient to vascularize the implantation site is in the range of 5 days to 90 days, e.g., 10 days to 60 days, including 10 days to 30 days.

In some cases, implanting the tissue graft may be performed in conjunction with another therapy, such as another surgical operation and/or administration of a drug. In some cases, the tissue graft is implanted at an implantation site after a surgical operation, e.g., to remove a tumor or malignant tissue from the implantation site.

Also provided herein is a method of regulating blood glucose level in an individual using a tissue graft made of a porous (e.g., macroporous and microporous) PCL scaffold, as described herein. The present method may include implanting a tissue graft that includes a porous (e.g., macroporous and microporous) polymeric scaffold, as described herein, and insulin-secreting cells encapsulated in the pores (e.g., macropores) of the PCL scaffold, as described herein, into an implantation site (e.g., a subcutaneous site) of a host individual, to maintain normoglycemia in the individual. The individual may be suffering from dysregulation of blood glucose, and may have, e.g., type 1 or type 2 diabetes, pre-diabetes, or hyperglycemia. The insulin-secreting cells may be any suitable insulin-secreting cells, as described above. The tissue graft may include any suitable number of cells, as described above, and in some cases includes $10^5$ to $10^9$ cells, e.g., $10^6$ to $10^8$ cells.

The present method may further include preparing the tissue graft by culturing the insulin-secreting cells on the polymeric scaffold, as described herein, to encapsulate the insulin-secreting cells in the macropores of the scaffold.

Utility

The present porous scaffold and tissue graft find many uses where it is desirable to transplant a population of therapeutic cells into an individual to treat a condition, e.g., a disease. As described herein, a variety of types of therapeutic cells (e.g., cells that secrete a hormone or enzyme, cytotoxic cells targeting a tumor, etc.) can be loaded into the porous scaffold, which provides a microenvironment conducive for survival, growth and functional activity of the therapeutic cells in an in vivo environment of the transplant host. The scaffold promotes vascularization, and minimizes foreign body responses, such as fibrosis at the site of implantation.

In some cases, where the therapeutic cells substantially remain in the tissue graft when implanted in the host tissue, the therapeutic cells may be removed, if necessary, by removing the entire tissue graft. In such cases, the polymeric scaffold may be designed (e.g., by providing an appropriate porosity, polymer molecular weight, etc.) to degrade at a sufficiently slow rate to retain the therapeutic cells in the scaffold over the desired duration of time.

Kits

Also provided herein is a kit that includes the present porous, polymeric scaffold and that finds use in performing methods of the present disclosure. The kit may also include a packaging that includes a compartment, e.g., a sterile compartment, for holding the scaffold. The packaging may be any suitable packaging for holding the present scaffold. Examples of packaging and methods of packaging are described in, e.g., U.S. Pat. Nos. 3,755,042, 4,482,053, 4,750,619; U.S. App. Pub. Nos. 20050268573, 20100133133, each of which are incorporated herein by reference.

In some cases, the present kit further contains cells, e.g., therapeutic cells, or a precursor thereof, suitable for forming a tissue graft, as described herein. In some embodiments, the cells are encapsulated within the pores (e.g., macropores) of the PCL scaffold, thereby forming tissue graft.

In some cases, the polymeric scaffold or tissue graft in the packaging includes an active agent. The different components of the kit may be provided in separate containers, as appropriate.

The present kit may also include instructions for using the present porous, polymeric scaffold and/or tissue graft, and for using the same. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal(ly); s.c., subcutaneous(ly); and the like.

Example 1: Fabrication of a Porous Polycaprolactone (PCL) Scaffold

A macroporous polycaprolactone (PCL) scaffold was fabricated using a solvent casting porogen leaching (SCPL) technique (FIG. 1). 2,2,2-Trifluoroethanol (TFE) was used as a solvent to dissolve PCL with overnight heating in a water bath at 70° C. After preparation of the PCL solution (75 mg/mL; ~7.5 w/v %), varied amounts (4~10 g) of sodium chloride (NaCl) was added to create a supersaturated solution. The PCL/NaCl solution was then cast onto a silicon wafer using a spin coater. Overnight evaporation of the TFE solvent produced a PCL scaffold with embedded NaCl crystals (upper left image of FIG. 2, "pre-leaching"). To remove the NaCl and give the scaffold porosity, the NaCl crystals were leached for 5-7 days in distilled water that was changed daily. After complete leaching of the NaCl, the scaffold was visibly more porous (lower left image in FIG. 2, "post-leaching"). Scanning electron microscopy imaging of the leached PCL scaffold revealed the presence of both macropores (~100~300 μm diameter) and micropores (~5~20 μm diameter).

Figure 3:
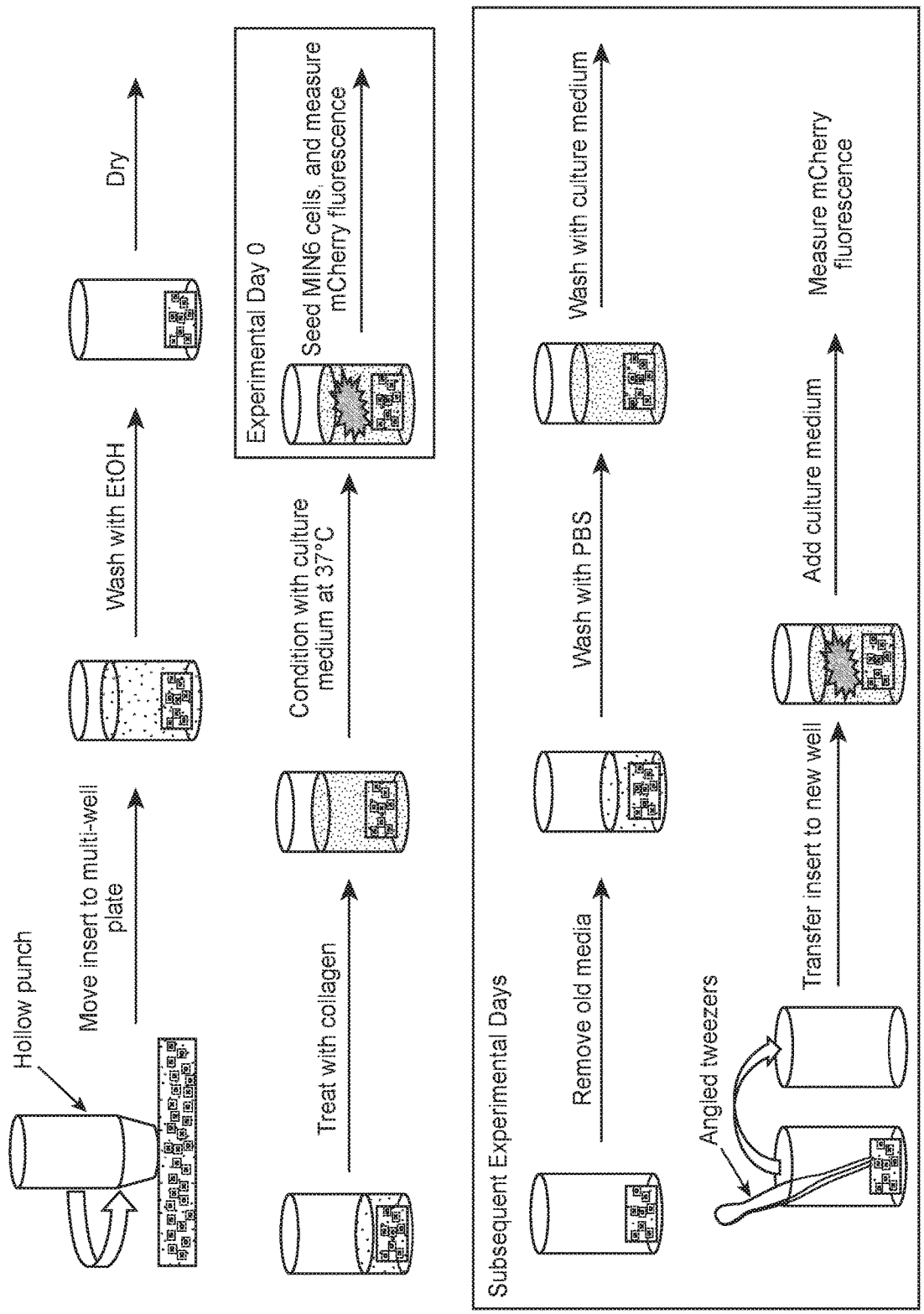
FIG. 3 is a schematic diagram depicting a method of preparing a porous PCL scaffold for loading with cells, and loading and culturing the cells, according to embodiments of the present disclosure.

Example 2: Incorporating and Culturing Pancreatic Beta Cells in a Porous PCL Scaffold To test the ability of the macroporous PCL scaffold to support cellular growth and function, pancreatic beta cell lines MIN6 cells were seeded into the scaffold and monitored for growth and function. Following fabrication of a large PCL scaffold, individual scaffold inserts were prepared to seed with MIN6 cells in wells of a 48-well plate. Briefly, scaffold inserts were prepared using a hollow punch, sterilized with EtOH, collagen coated, and conditioned with culture media (FIG. 3). The prepared inserts were seeded with 200,000 MIN6 cells, which constitutively expressed mCherry so that their growth could be measured by monitoring fluorescence. On subsequent experimental days, old media was removed, the scaffold was washed, the scaffold was transferred to a new well, fresh media was added, and the mCherry fluorescence was measured with a plate reader to quantify cellular growth.

Figure 4A:
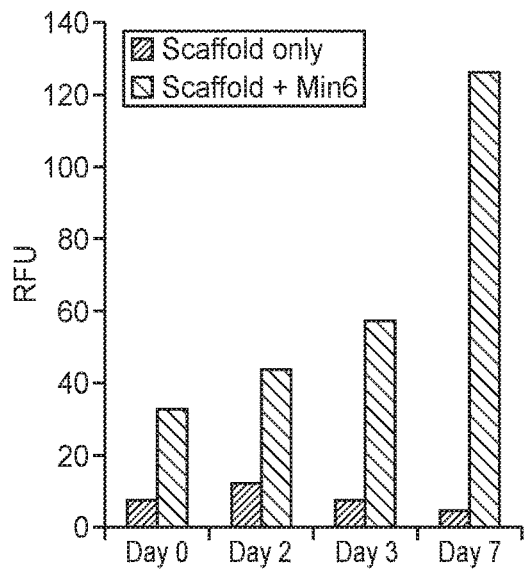
FIGS. 4A and 4B are a collection of graphs showing expansion over time of MIN6 pancreatic beta cell line cells seeded on a porous PCL scaffold, according to embodiments of the present disclosure.
Figure 4B:
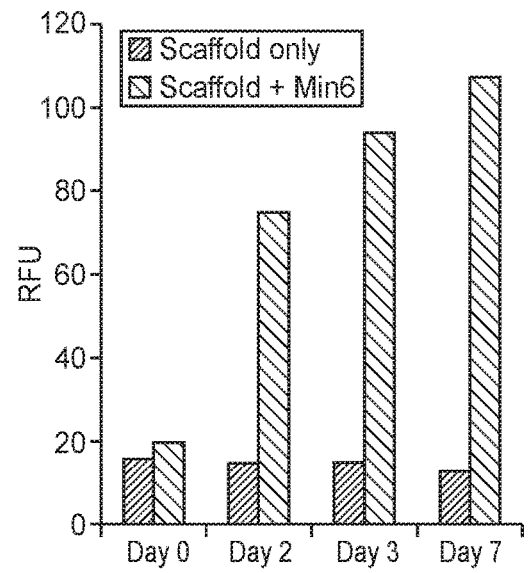

In one experiment, scaffolds seeded with MIN6 cells or left empty and the mCherry fluorescence was measured for one week. mCherry fluorescence measurements taken from both the top of the wells (FIG. 4A) and the bottom of the wells (FIG. 4B) showed that mCherry fluorescence, as a marker of cell growth, increased over time in the scaffold+MIN6 condition but not in the scaffold only condition. This experiment was the first demonstration that the macroporous PCL scaffold was able to support cellular growth.

In another experiment, MIN6 cells were seeded into macroporous PCL scaffold or onto regular tissue culture plastic (PS) and mCherry fluorescence was monitored for 12 days. In both the PCL scaffold and the PS conditions the mCherry fluorescence intensity increased over time, but the increase was more dramatic for MIN6 cells cultured in the PCL scaffold (FIG. 5, n=8). Following 12 days of growth, MIN6-seeded scaffolds were fixed and sectioned for imaging. The gross morphology of an intact macroporous PCL scaffold was evaluated using bright field microscopy, and imaging showed large macropores whose surfaces are littered with smaller micropores (FIG. 6A). Bright field microscopy imaging of fixed and sectioned MIN6-seeded scaffolds showed that the cells attached to the surface of the scaffold around the edges of the macropores (FIG. 6B). These results indicate that not only can the macroporous PCL scaffold be used to support cellular growth, but also that the PCL scaffold may be superior to regular PS for supporting the expansion of MIN6 cells.

FIGS. 6A-6B: (FIG. 6A) A bright field microscopy image of an intact PCL scaffold showing macropores whose surfaces are covered with micropores. (FIG. 6B) A bright field microscopy image of a PCL scaffold that had been seeded with MIN6 cells, fixed, and sectioned. The cross-section image of the scaffold shows a magnified macropore with MIN6 cells (small circles) attached to its surface, demonstrating the ability of cells to infiltrate and populate the scaffold.

Figure 7B:
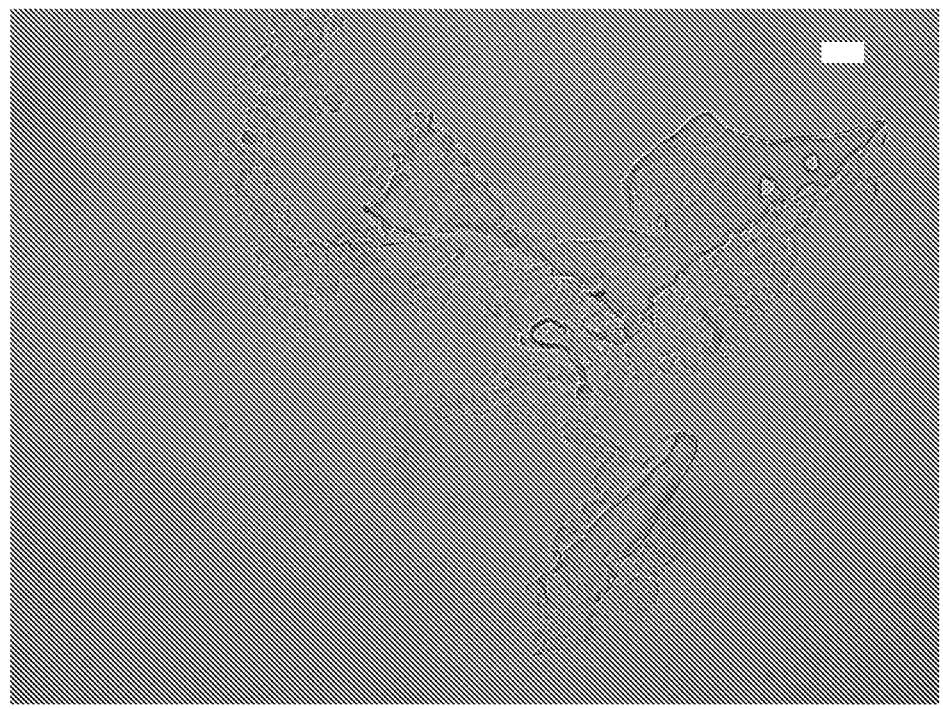

Following the 12 day growth experiment described above, fixed and sectioned scaffolds were processed for immunofluorescence (IF) analysis. Sectioned scaffolds were stained with a mouse anti-insulin antibody to detect insulin producing cells and DAPI mark nuclei. IF imaging showed colocalization of mCherry (MIN6 cell bodies) and the anti-insulin antibody (FIGS. 7A and 7B), which shows that MIN6 cells cultured on the PCL scaffold are able to produce insulin. The ability of pancreatic beta cells to produce insulin is critical to their function, but this ability can be loss with extended in vitro culture.

Figure 8:
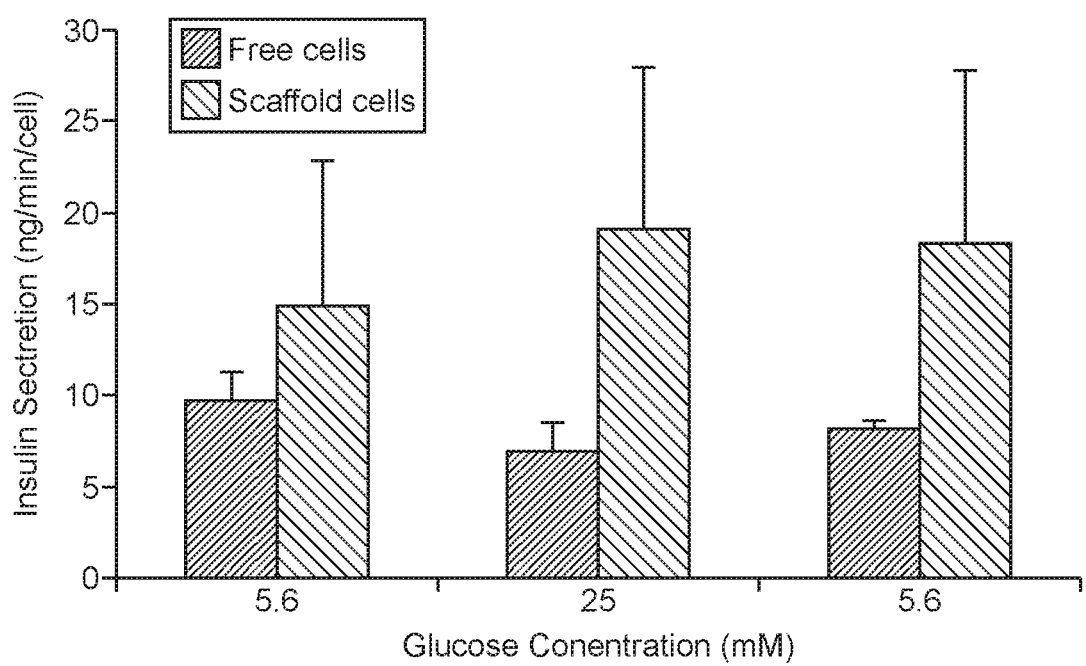
FIG. 8 is a graph showing glucose-stimulated insulin secretion from MIN6 cells cultured on different substrates, according to embodiments of the present disclosure.

To further test the ability of PCL scaffold-cultured MIN6 cells to produce insulin, scaffold-cultured and PS-cultured MIN6 cells were assayed for glucose-stimulated insulin secretion. Initial testing suggests that scaffold-cultured MIN6 cells are able to produce more insulin than PS-cultured MIN6 cells (FIG. 8). Together, these results indicate that the macroporous PCL scaffold was able to support the insulin-secreting function of pancreatic beta cell line MIN6 cells in vitro, and that the insulin secretion of scaffold-cultured cells may be superior to insulin secretion of PS-cultured cells.

Example 3: Maintenance of Normoglycemia Following Subcutaneous Transplantation of Human Stem Cell-Derived Insulin Producing Cells (SCIPCs) in a Diabetic Murine Model Materials and Methods:

Prevascularization of a subcutaneous transplant site was achieved by implantation of a 1.5 cm-diameter polycaprolactone (PCL) or polypropylene (PP) thin-film disc to the dorsum of NSG mice for a duration of 10-21 days. At time of transplant, thin-film discs were explanted and 2-3 million SCIPCs were delivered via a PCL scaffold to prevascularized sites (PCL=6, PP=6) or to naïve NSG mice as controls (n=3). SCIPCs were differentiated with constitutive expression of firefly luciferase by this reporter line allowing for in vivo real-time bioluminescence imaging of viability. SCIPC grafts were serially imaged for viability until 28 days post-transplant. At 28 days, diabetes was induced by serial dosing of streptozotocin (Teva Parenteral Medicines, Irvine, Calif.), with non-transplanted NSG mice serving as controls (n=3). Mouse blood glucose levels were monitored three times weekly, with diabetes defined as 3 serial measurements over 250 mg/dL.

Results:

SCIPC grafts were able to maintain normoglycemia in a dose-dependent fashion, while all control mice became diabetic following STZ treatment. Prevascularization of the subcutaneous space with PCL or PP showed a trend toward improved graft survival (p=0.058 and 0.087, respectively), while no significant difference was seen between use of PCL versus PP thin-film discs for prevascularization (p=0.690).

Example 4: Macroporous Synthetic 3D Polymer Scaffolds for Cell Therapy in Type 1 Diabetes A synthetic polymer matrix was used to remodel the microenvironment of the islet graft site. Through in vitro studies, the maximal packing density of islets within the scaffolds was characterized as well as glucose stimulated insulin secretion from islets. Finally, immunomodulatory strategies were demonstrated that could be combined with a scaffold material to overcome immune mediated graft rejection.

An alternative strategy to delivering islet replacement therapy was used by utilizing a highly tunable synthetic polymer scaffold to remodel the microenvironment of the islet transplant site. A microporous scaffold made up of a synthetic polycaprolactone polymer material with pore sizes ranging from 150 to 250 micrometers was designed. The size range of pore size was fabricated to allow for efficient infiltration and containment of islets which have an average diameter of 150 micrometers. Templated microwells measuring 500 micrometers were introduced onto the loading surface of the polymer scaffolds to improve the distribution of the seeded cells. The final matrix scaffold was porous and flexible and could be cut to customized shapes to adhere to the desired transplant site and environment.

The ability of a polymer scaffold to improve the microenvironmental niche was demonstrated for adequate islet cell survival and function. Through a series of in vitro and in vivo experiments, it was shown that islet cells packed within the scaffold preserve their insulin secretion kinetics in response to glucose challenge. Moreover, islet-scaffold constructs transplanted into syngeneic diabetic mice were successful in lowering blood glucose.

Materials and Methods:
Laser Etched Acrylic Mold

A honeycomb tiled template composed of 500 micrometer circles spaced 50 micrometers apart was illustrated in adobe's illustrator software. The illustration was imported into ULS Laser Cutter system at the UCSF Center for Advanced Technology to produced etched patterns in acrylic slabs measuring. The acrylic mold is approximately 4×2 inches with honeycomb pattern of 500 micrometer wells neatly patterned across the surface. The final acrylic slab was cleaned by sonicating in a beaker filled with deionized water and isopropryl alcohol (10% v/v).

Polydimethylsiloxane (PDMS) Negative Template Mold

Polydimethylsiloxane (Sylgard 184) was cast onto the laser etched acrylic mold. PDMS was crosslinked by adding 10% initiator solution and baked in 50° C. vacuum pressured oven overnight. The PDMS was then peeled from the acrylic mold to yield the final negative template mold.

3D Polymer Scaffold Fabrication 3D polymer scaffolds were fabricated using polycaprolactone combined with a salt leaching method. Briefly, 80 kDa polycaprolactone and 2 kDa polyethylene glycol was dissolved in trifluoroethanol at a concentration of 100 mg/mL. The mixture polymer solution was sonicated for 30 minutes using a water bath sonicator to achieve a homogeneous solution. Salt was added to the polymer solution at 10 g/mL and agitated to form a slurry. The polymer-salt slurry was then cast onto the PDMS negative template mold and allowed to dry in a chemical hood overnight. The final polymer-salt-PDMS construct was submerged in a beaker filled with deionized water to allow the salt to leach out of the scaffold. The final polymer scaffold is then peeled off of the PDMS.

Glucose Stimulated Insulin Secretion

An automated perifusion (Biorep) was used to measure the insulin secretion kinetics of islets in response exposure to varying glucose concentration buffers. Free islets were loaded into the bioreactor chambers by first packing polyacrylamide beads into the chambers before depositing 100 islet clusters. Scaffolds were cut to fit the diameter of the bioreactor and pre-loaded with 100 islets before being inserted into the bioreactor chamber. The flow rate of the perifusion system was set to 100 µL/min and perfusates from each bioreactor chamber was collected every 150 seconds in a 96 well plate. Finally, insulin concentrations from the perfusate were quantified using a commercial ELISA kit (Mercodia).

Surface Protein Conjugation

A trilayer PCL film was fabricated. Each layer was then spin coated at 500 rpm for 45 seconds. Bottom layer: 10 mg/mL of PMPI-PCL in TFE. Approximately 0.5 mL of mixture was added onto wafer. After spin coating, layer dried in under 1 minute. Middle layer: 100 mg/mL of PCL in TFE. Approximately 2 mL of mixture was added onto wafer. After spin coating, layer dried in about 5 minutes. Top layer: 10 mg/mL of PMPI-PCL in TFE. Approximately 2 mL of mixture was added onto wafer. After spin coating, layer dried in 2-3 minutes.

Traut's reagent was then used to thiol-activate EGFP. A stock solution of pH 8.0 PBS was prepared by adjusting pH 7 PBS by adding NaOH drop by drop. 3 mM EDTA was added. Stock EGFP solution was diluted in pH 8.0 PBS, 3 mM EDTA buffer. Traut's reagent was added (diluted to 14 mM in water or PBS) so that [Traut's reagent]=10 [GFP] (concentrations). The solution was set for 1 hour at RT, and was kept covered. While reaction tube was incubating, a desalting column was equilibrated using the pH 8.0 PBS, 3 mM EDTA buffer. The reaction mixture was fun through desalting column. Both maleimide-doped and control films were left overnight, adding 500 uL of the eGFP solutions. The films were kept covered and at RT on a shaker.

Quantification of Conjugated Protein

Fluorescence of films were measured once taken out of solution using excitation 485 nm, emission 515 nm. Using a standard curve of serial dilution of eGFP, the mass could be calculated.

Desorption of Surface Protein

Protein adsorbed material was immersed in 1% SDS for 2 hours on a shaker at room temperature. Measurement of fluorescent protein on films was performed using a fluorimeter. Films were sonicated in 1% SDS for 5 minutes twice. Quantification of protein mass on surface was performed using a BCA assay on both desorption buffer fractions as well as directly on the film.

Cell Culture

Isolation of mouse islets was performed using existing methods. Islets and MING cells were cultured in RPMI 1640 supplemented with 10% (v/v) fetal bovine serum. Undifferentiated Mel1$^{INS-GFP}$ cells were maintained on mouse embryo fibroblast feeder layers (Milli-pore) in hESC media using existing methods. Suspension-based direct differentiations to generate hES-βC were carried out as described using existing methods with improvements to the last stage.

Gene Targeting of Mel1$^{INS-GFP}$ Cells

To generate a cell line that expresses a constitutive firefly luciferase gene a recently known gene targeting approach was employed of the insulated human AAVS1 loci employing TALENs. Briefly, a 6332 bp DNA piece containing all bacterial components was amplified, both homologies to the human AAVS1 loci, as well as the puromycin resistance gene from the Puro-Cas9 donor plasmid (Addgene #58409) and cloned a fragment consisting of a peptide cleavage site T2A, followed by the firefly luciferase gene and a poly A sequence in, to re-circulate the DNA piece. The resulting plasmid, termed Puro-T2A-Luc donor, was sequence verified by sanger sequencing. Confluent Mel1$^{INS\text{-}GFP}$ were dissociated to single cells and approximately 8.0×106 cells were mixed with 5 ug of each of the TALEN plasmids and 20 µg of the Puro-T2A-Luc donor in a 0.4 cm gap electrocuvette (Biorad). Cells were electroporated using a GenePulser (Biorad) using an exponential decay with 250V and 500 uF settings. Targeted cells were plated on DR4 resistant MEFs and clones were selected with 0.5 µg/ml Puromycin for 4 days. After 11-12 days, individual clones were manually picked and expanded before freeze down and genomic DNA analysis. gDNA was analyzed with primers for WT and correct Puro integration. WT/Puro Forward: CCG GAA CTC TGC CCT CTA AC (SEQ ID NO:1), WT Reverse: AGA TGG CTC CAG GAA ATG GG (SEQ ID NO:2), Puro Reverse: GTG GGC TTG TAC TCG GTC AT (SEQ ID NO:3). Mel1$^{INS\text{-}GFP,\ AAVS1\text{-}Luc}$ line #3 was used for direct differentiation experiments.

Mice

NOD.Cg-Prkdcscid Il2rgtm1Wjl/SzJ mice (NSG) and C57BL/6J mice were obtained from Jackson Laboratories. Mice used in this study were maintained according to protocols approved by the University of California, San Francisco Committee on Laboratory Animal Resource Center. For kidney capsule grafts, approximately 2.0×10$^6$ hESC-differentiated cells in clusters were transplanted. For subcutaneous grafts, approximately 2.0×10$^6$ hESC-differentiated cell sin clusters were transplanted on the left dorsal aspect of the animal. For epidydimal fat pad grafts with and without scaffolds, a small incision was made to access the epidydimal fat pad and approximately 200 islet clusters were inserted before suturing up the animal.

In Vivo Bioluminescence Imaging

Survival of cells in vivo was assessed by monitoring luciferase activity using a Xenogene IVIS 200 imaging system (PerkinElmer). The animals transplanted with hSC-βC cells were injected IP with D-luciferin solution (Goldbio, St. Louis, Mo.) at the dose of 150 mg/kg 5 min before imaging to capture the peak in bioluminescent intensity. The mice were anesthetized with an isoflurane mixture (2% in 98% 02) and imaged by using a Xenogen IVIS 200 imaging system. Bioluminescence images were acquired for 3 min and then analyzed using the Living Image analysis software (Xenogen, Alameda, Calif.). Regions of interest (ROI) were centered over the bioluminescence regions. Photons were counted within the ROI over the acquisition time. Adherence to the same imaging protocol ensured consistent signal detection on different days of in vivo imaging.

Results:

Fabrication of Templated 3D Polymer Scaffold

A 3D polymer scaffold was designed to facilitate the transplantation of islets in a manner that permits optimal packing of islets with better spatial distribution. The scaffolds were designed with stochastic macroporous structures that serve the function of allowing islets to embed within as well as the ingrowth of blood vessels to vascularize the islets. The transplanting islets were seeded on an organized matrix scaffold instead of direct delivery free islets.

Figure 11A:
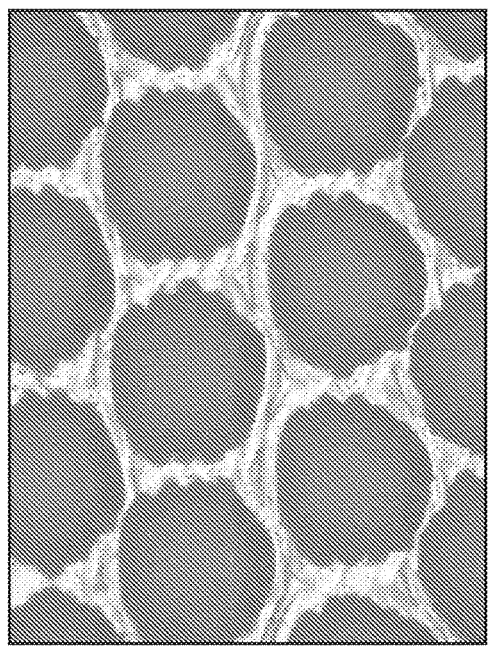
FIGS. 11A and 11B show a template fabrication for polymer scaffold, according to embodiments of the present disclosure.
Figure 11B:
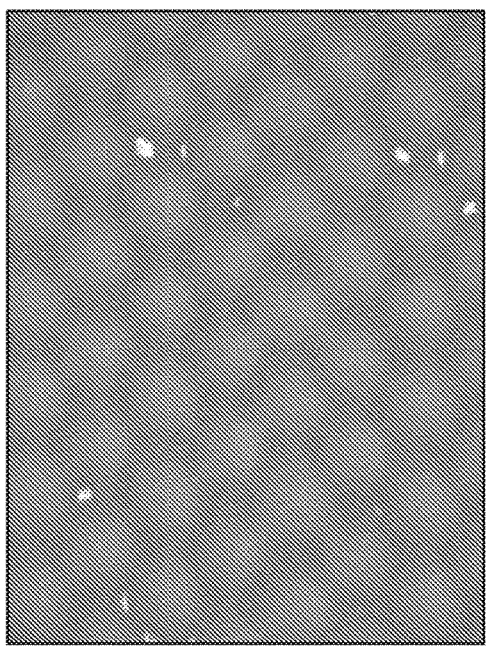

In order to produce a scaffold that better distributes seeded islets spatially with minimal aggregation, precise microwell structures were fabricated onto one surface of the polymer scaffold. Microwells measuring 500 microns in diameter were first etched into an acrylic mold using a laser cutter (FIG. 11A). Polydimethylsiloxane (PDMS) was then cast on to the templated acrylic and crosslinked to produce a negative mold consisting of 500 micron posts (FIG. 11B). Polycaprolactone and polyethylene glycol was dissolved in trifluoroethanol combined with potassium chloride salt crystals to form the polymer-porogen slurry (FIG. 1). Salt particles measuring between 150 to 250 microns were selected to match the approximate size of isolated mouse islets. The slurry was mixed thoroughly by agitation before cast onto the PDMS negative mold and allowed to dry overnight. Finally, porogens were leached out of the polymer scaffold using deionized water (FIG. 9A-E). The final polymer scaffold is approximately 1 mm thick consisting of 500 micron wells with interconnected pores measuring 150 to 250 microns.

Cell Loading Capacity and Viability within Polymer Scaffold

Figure 12A:
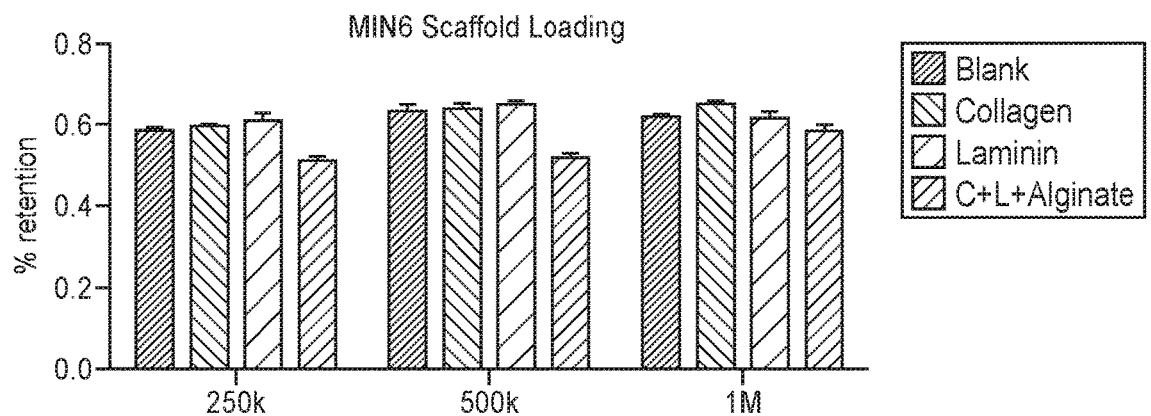
FIGS. 12A-12C show characterization of scaffold retention of single beta cells and islet clusters, according to embodiments of the present disclosure.

Single MIN6 cells were seeded onto the collagen, laminin, or collagen and laminin coated scaffolds at increasingly seeding densities. The cell-scaffold constructs were cultured overnight in complete cell culture medium before being transferred into new polystyrene wells and quantified for the amount of cell retaining. The experiment results showed that approximately 60% of the seeded cells were consistently retained regardless of initial seeding density or surface protein coating (FIG. 12A). Thus the scaffolds were sufficiently packed with enough beta cells to reach a therapeutic effect in vivo.

Figure 12B:
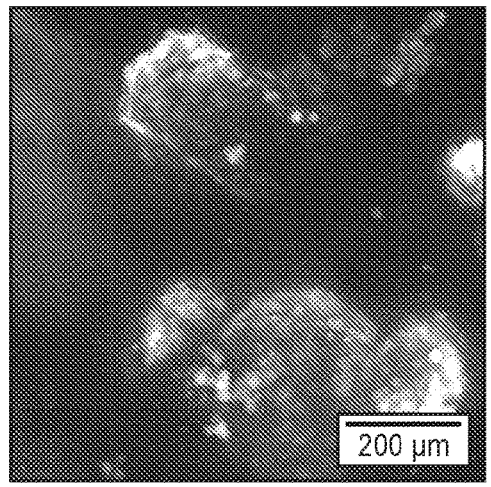
Figure 12C:
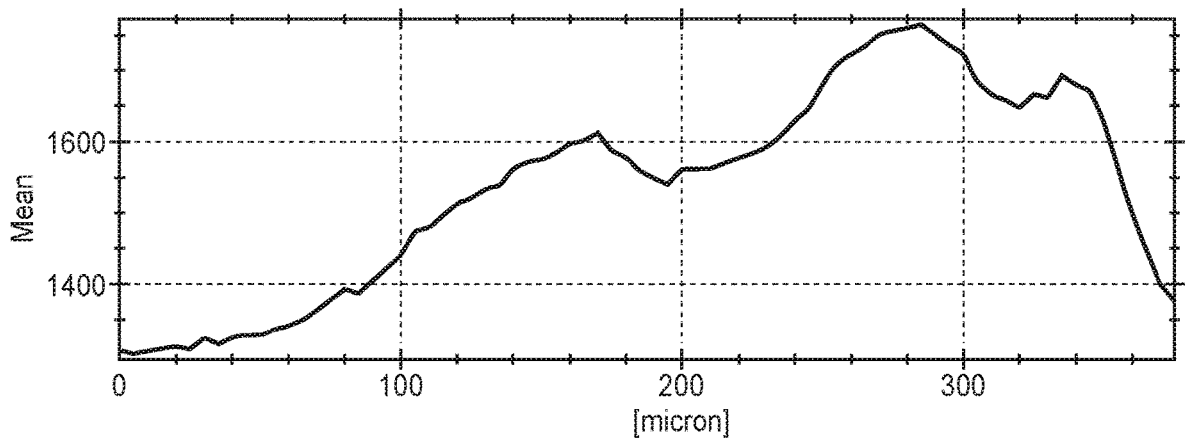
Figure 13B:
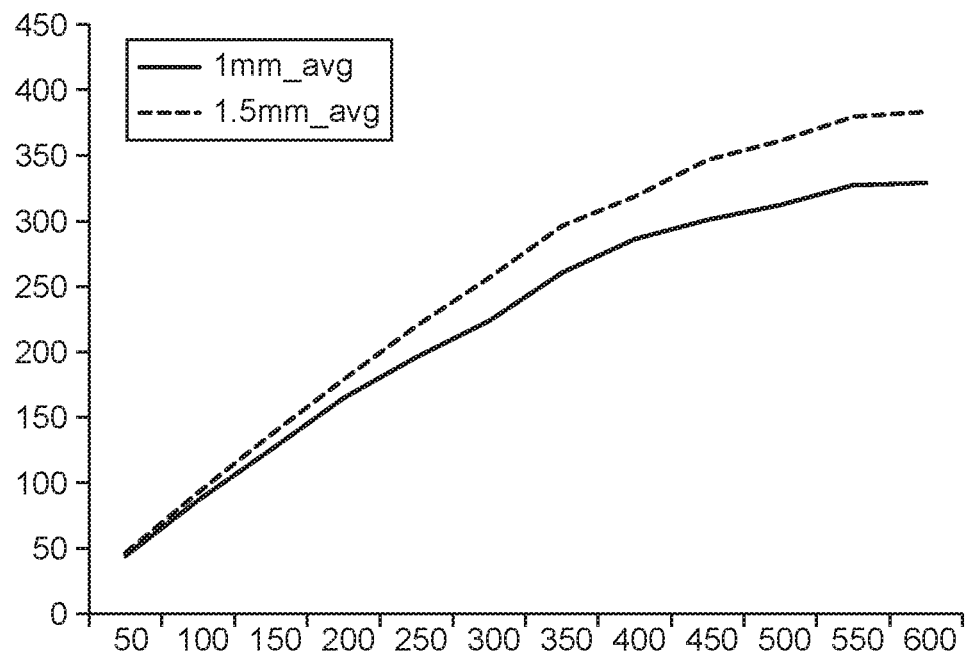
Figure 13C:
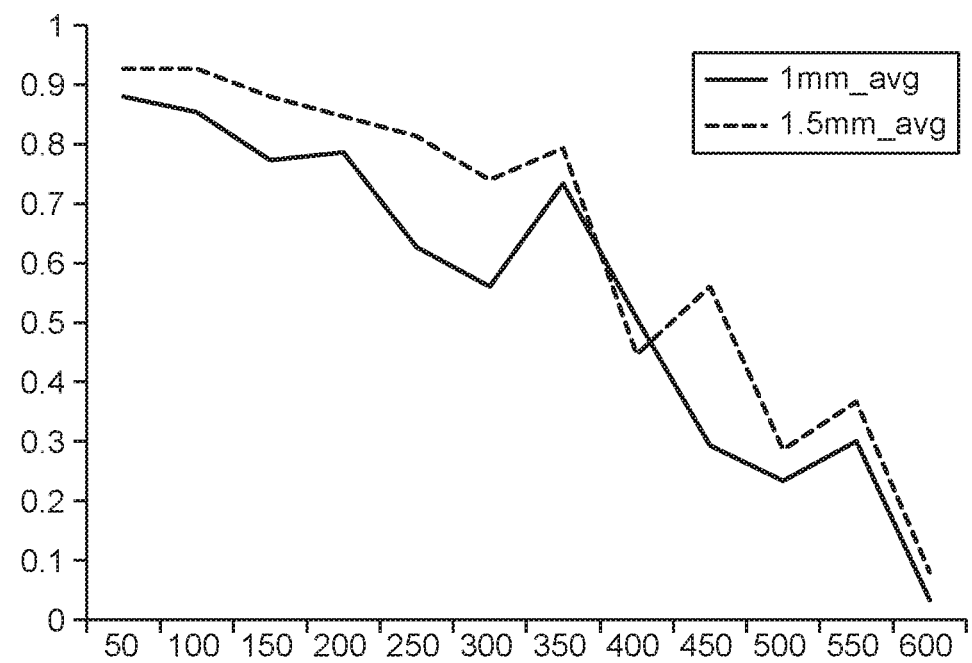

Next, the scaffolds were loaded with islets engineered with a luciferase reporter driven by the mouse insulin promoter. In this experiment, scaffolds with loaded with 100 islets and imaged by confocal microscopy. The results showed that islets do indeed infiltrate throughout the fully thickness of the scaffold as opposed to being merely seeding on the top surface (FIG. 12A-C). To further investigate and characterize the maximum loading capacity of each scaffold, PLGA microparticles measuring 150 micrometer in diameter were seeded, similar to the average size of islets. Confocal microscopy of microparticle loaded scaffolds showed infiltration throughout the z-axins or thickness of the matrix (FIG. 13A). Moreover, consistent with our hypothesis, the loading efficiency drops precipitously as we increase the loading density (FIG. 13B-C). The loading capacity was maximized at approximately 300 islet clusters for the 1 mm thick scaffold, and slightly higher at 350 islet clusters for the 1.5 mm thick scaffold (FIG. 13B). With each attempt to load 50 additional cluster into the scaffold, loading efficiency also dropped. A significant drop was observed when attempting to load up to 250 clusters and 350 clusters into the 1 mm scaffolds respectively (FIG. 2.5C).

Characterization of Viability and Function of Cells Loaded PCL Scaffolds

Figure 5A:
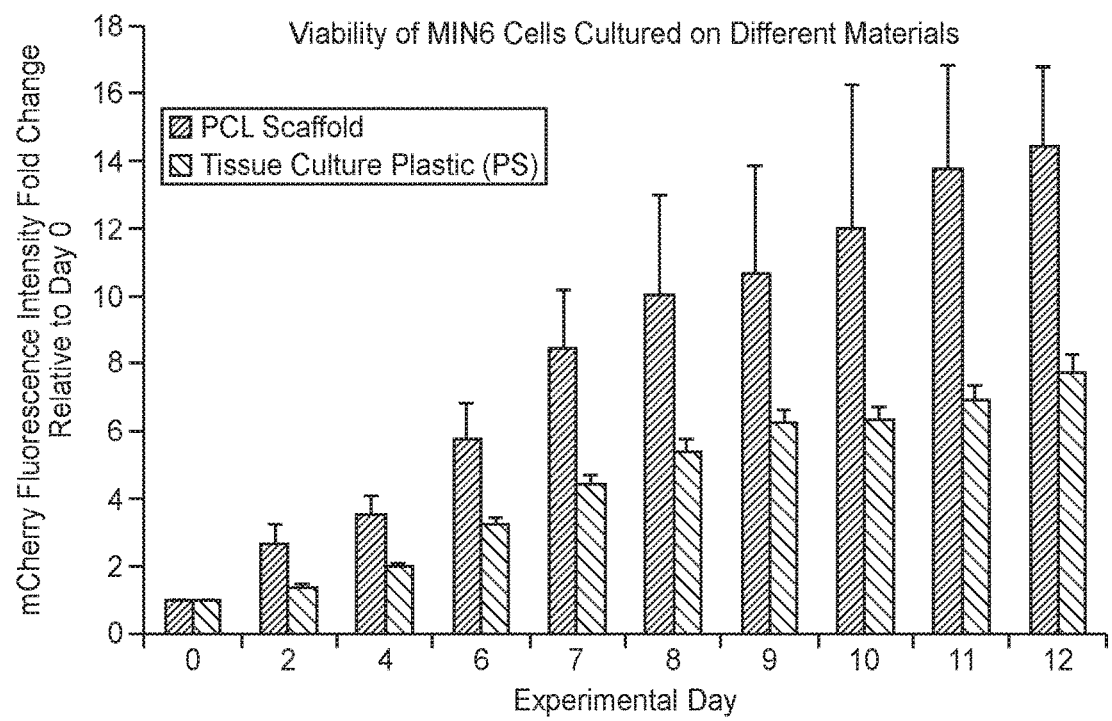
FIGS. 5A and 5B show viability of MIN6 cells cultured on different substrates and insulin secretion kinetics, according to embodiments of the present disclosure.
Figure 5B:
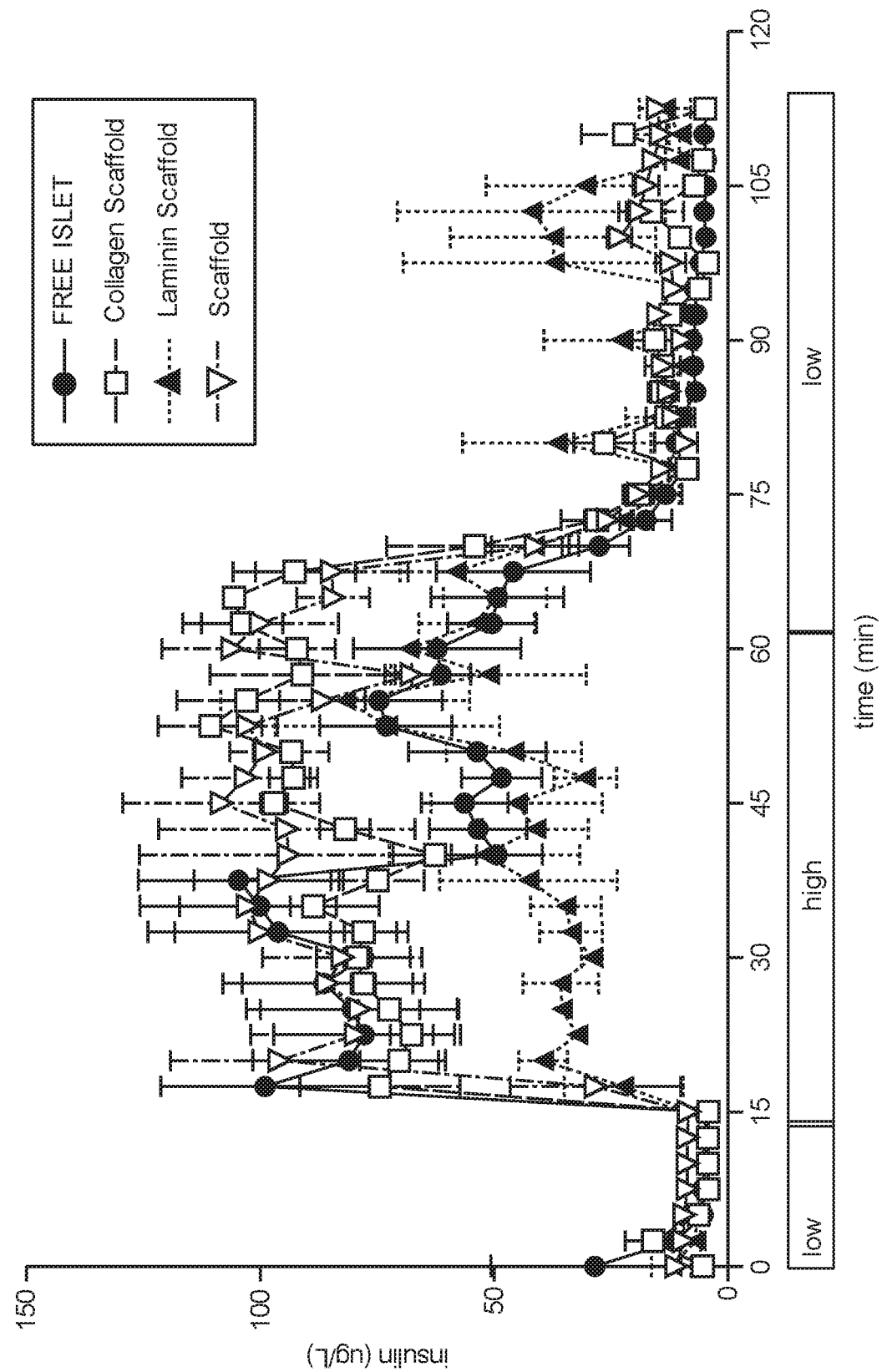

To investigate the viability of single cells in scaffold, mCherry—MIN6 cells were seeded onto PCL scaffolds or tissue culture treated plastic at 20,000 cells per 0.36 cm$^2$ area. Fluorescent intensity of mCherry cells were measured daily and observed elevated cell proliferation on the PCL scaffolds (FIG. 5A). PCL scaffolds through its 3D architecture may have significantly increased the surface area for Min6 cell adhesion compared to flat 2D tissue culture surfaces. The function of mature primary mouse islets loaded in scaffolds coated with collagen, laminin, or blank were further assessed. 50 islets were loaded in each scaffold or control and utilized an automated islet perifusion system to flow low and high glucose concentration buffer continuously through scaffolds a precise flow rates. Perfusate was collected every 2.5 minutes for each sample. The experimental results suggest that uncoated scaffolds and collagen coated scaffolds performed non-inferiorly when compared to free islets. More specifically, there was no delay in insulin secretion kinetics when islets were transitioned in between different glucose concentration buffers (FIG. 5B). Although it is worth noting that islets seeded on scaffolds did not produce an expected biphasic insulin secretion response when stimulated under high glucose media as seen in the free islet controls (FIG. 5B). Nevertheless, the results of this study confirmed that glucose and insulin diffusion kinetics were uninhibited by the scaffold material when compared to free islets.

Characterization of Scaffold In Vivo Transplants and Reversal of Diabetes

Figure 10A:
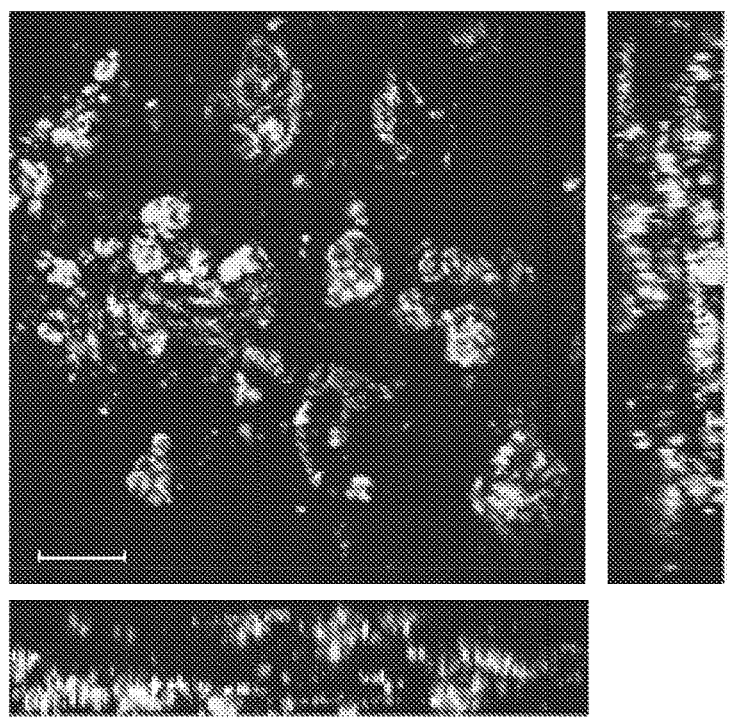
Figure 10B:
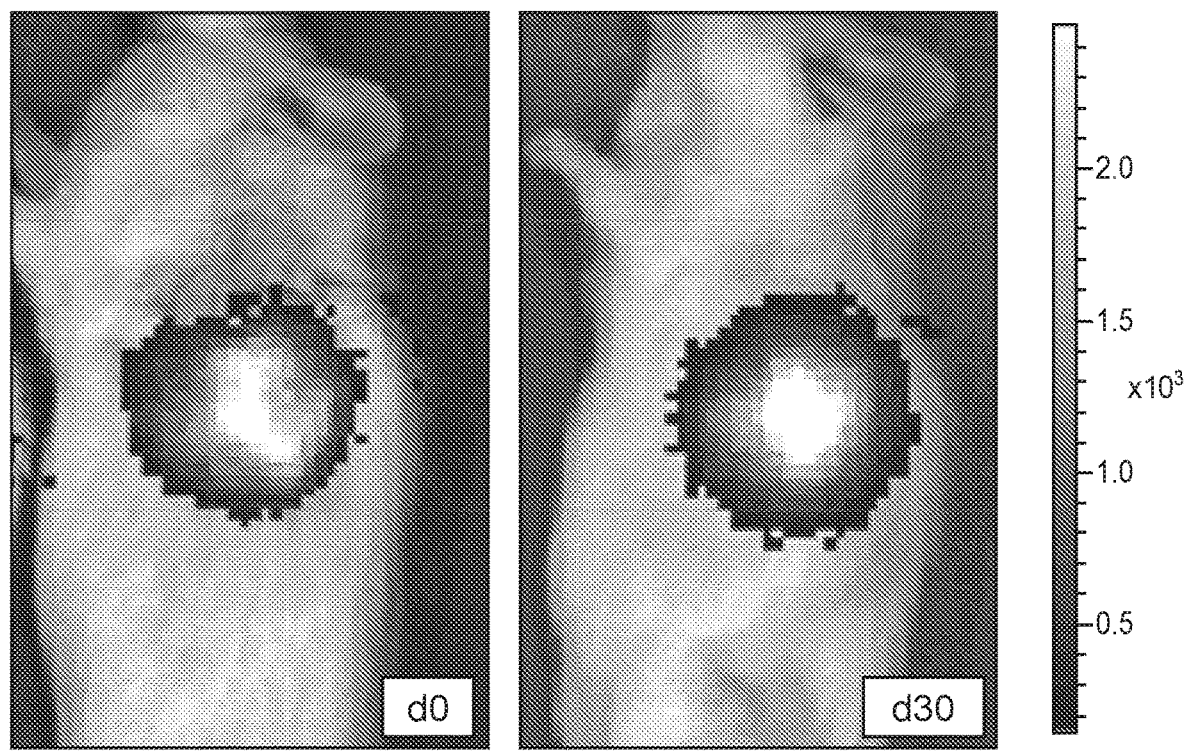
Figure 10C:
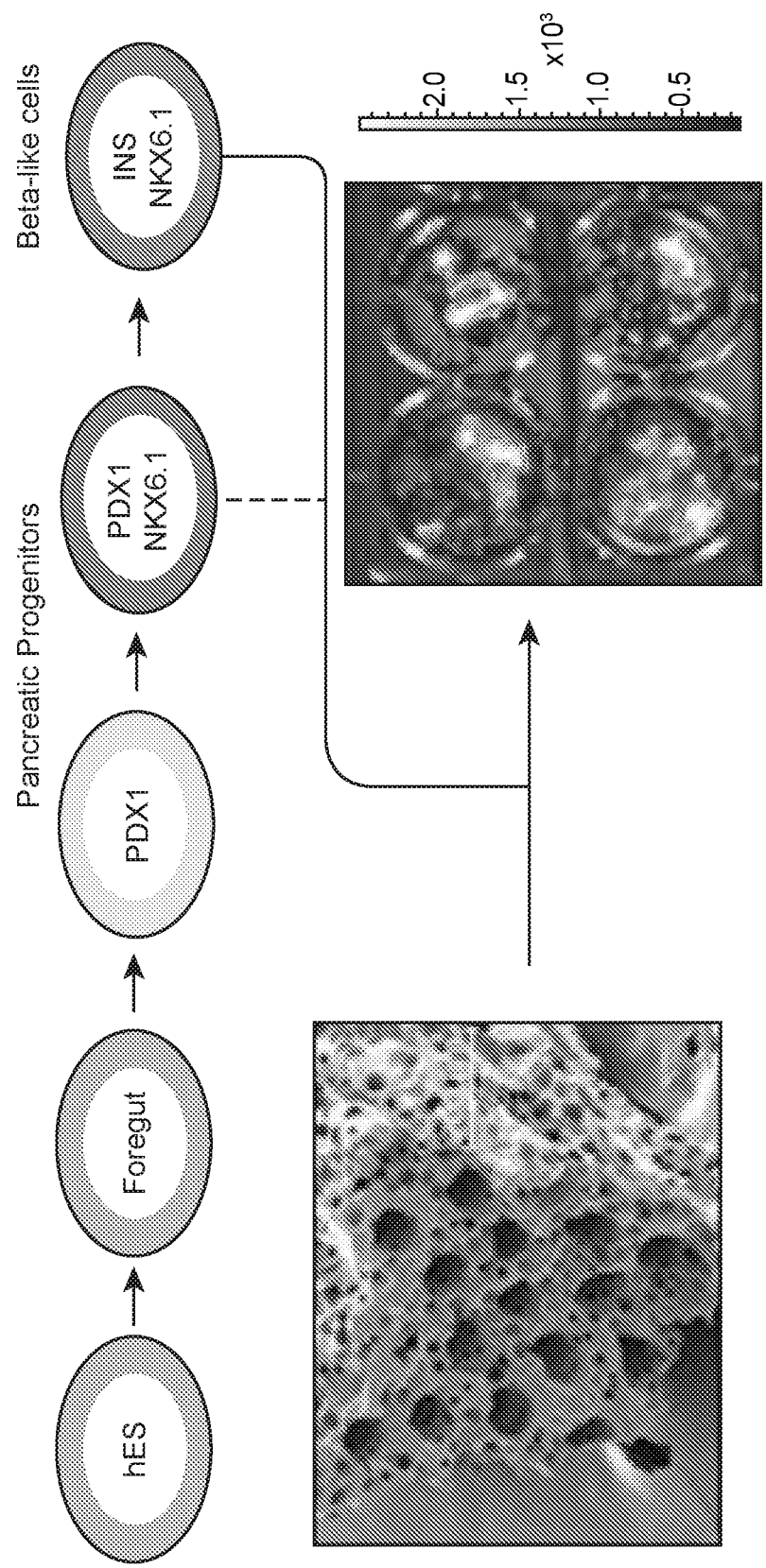
Figure 10E:
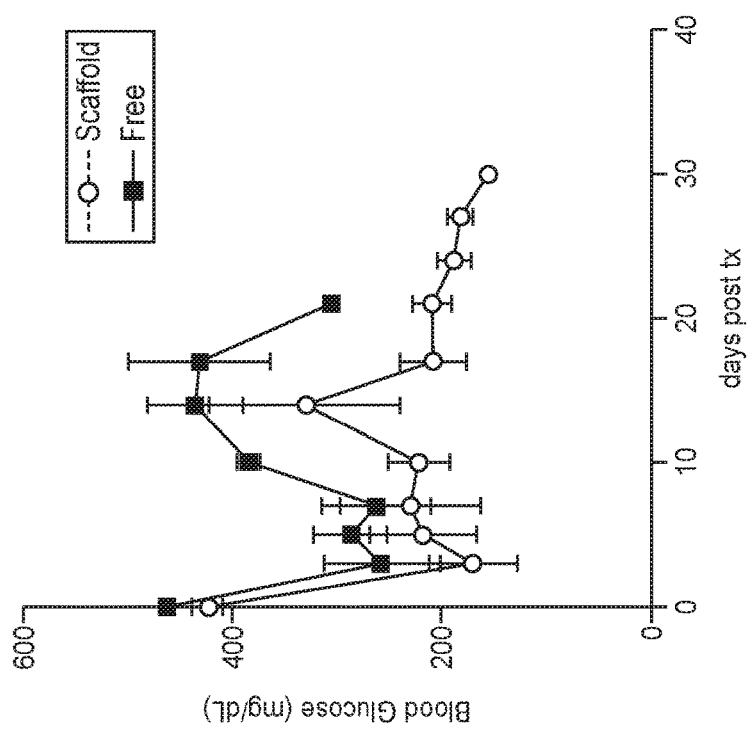

Although scaffolds loaded with islets have been demonstrated favorable loading capacity and glucose stimulated insulin secretion kinetics, the translation to in vivo therapeutic response is still unclear. To further elucidate the therapeutic potential of the islet-scaffold construct and demonstrate that it may be superior to loading free islets, in vivo transplants were performed. First, stem cell derived beta-like cell clusters consisting of pancreatic progenitors and mature-beta like cells were pre-seeded onto scaffolds and transplanted into the subcutaneous space in NSG mice (FIG. 10A-C). The results showed that cells infiltrated throughout the entire volume of the scaffolds and luciferase reporter indicated viable cells both in vitro and in vivo on day of transplant and also 30 days post-transplant. Luciferase based in vivo images suggested that viability signal was stable throughout the course of 30 days which compares favorably to historical free islet only controls transplanted subcutaneously or in the kidney capsule where the bioluminescence intensity is reduced by more than 95%, and 80% respectively by day 20 (FIG. 10D-E) To assess whether the improvement in cell survival translates into added therapeutic efficacy, mature mouse islets isolated from wildtype C57B6/J mice were transplanted into the epidydimal fat pads of syngeneic diabetic mice. The experimental results indicated that islets transplanted with or without scaffolds were both able to reverse diabetes within 3 days of transplantation measured by blood glucose under 250 mg/dL. However, in animals with islets transplanted without scaffolds, blood glucose rose after a week and failed to continue to control blood glucose levels. However, substantial beta cell mass has been lost due to cell death following one week of transplantation. In contrast, diabetic mice that received islets in scaffold transplants continued to have controlled blood glucose levels under 250 mg/dL up to 30 days after transplantation (FIG. 10E). This was shown in this series of studies that PCL scaffolds may convert previously unfavorable transplant sites into more advantageous microenvironments that offer improved cell survival and therapeutic efficacy in controlling elevated blood glucose.

Immunomodulatory Materials to Deliver Local Immune Suppression

Figure 14A:
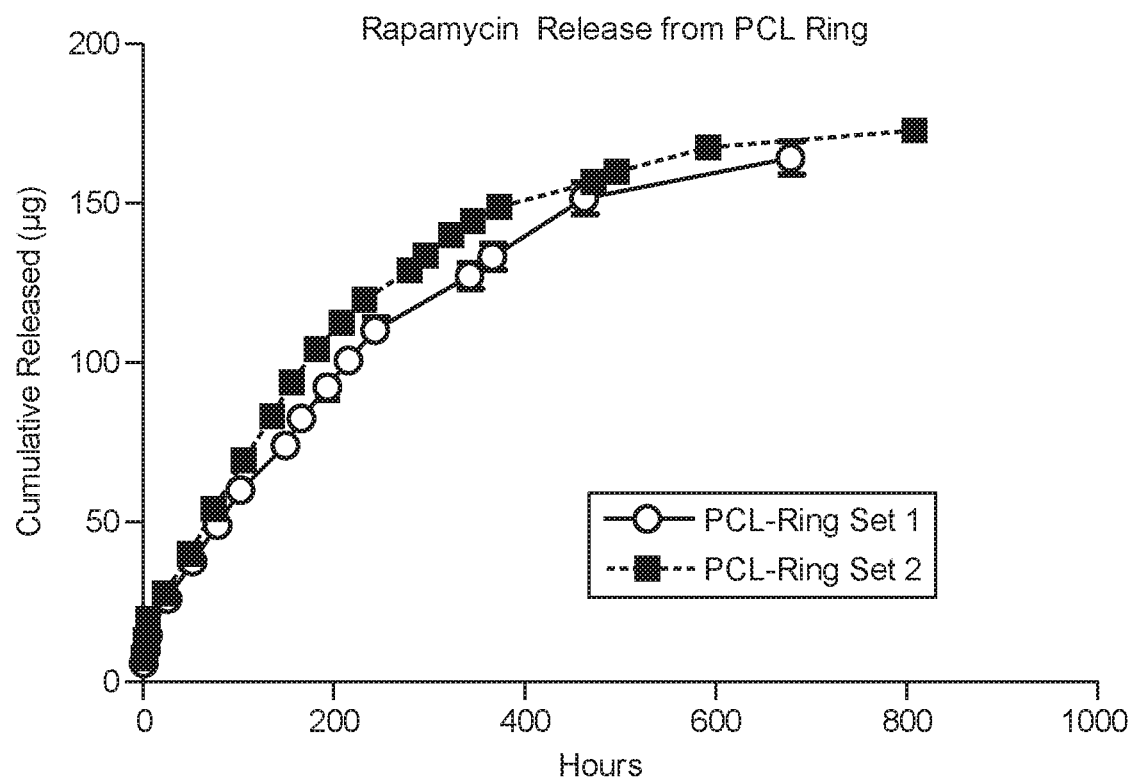
FIGS. 14A and 14B show local release of Rapamycin from nonporous PCL ring, according to embodiments of the present disclosure.
Figure 14B:
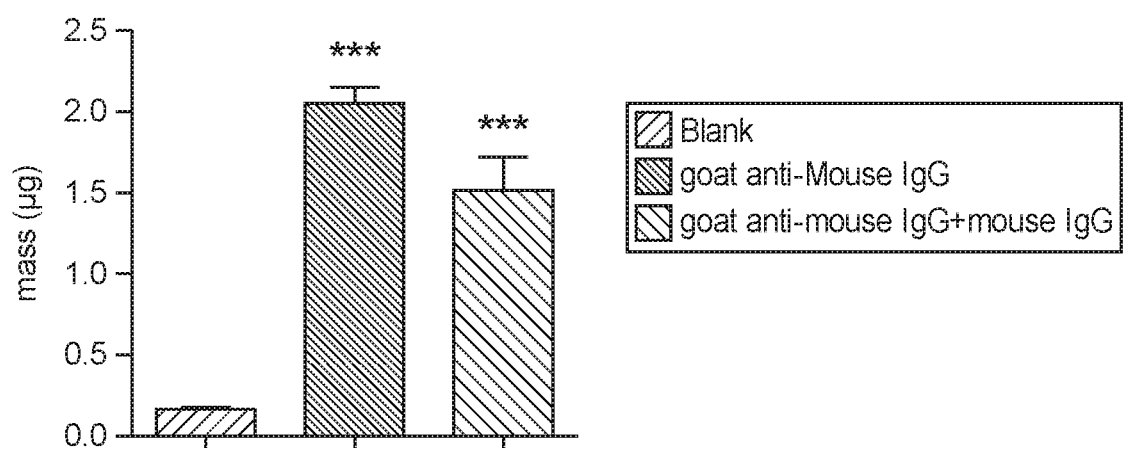

Another approach that entails reprogramming the local immune environment through the release of drugs to inhibit immune response locally was described. Rapamycin is an mTOR inhibitor that inhibits T cell proliferation and function. As a hydrophobic small molecule drug, it can be fully intercalated within the polymer matrix of polycaprolactone and dissolved within organic solvents. Controlled continuous release of rapamycin intercalated into a bulk PCL ring was demonstrated (FIG. 14A). In addition, antibodies may be conjugated onto the surface of polycaprolactone scaffolds using NHSS-EDC chemistry (FIG. 14B). Neutralizing antibodies against specific proinflammatory cytokines such as interferon-gamma or tumor necrosis factor-alpha may be immobilized onto the scaffold surface. This provides a plausible alternative to complete immune-isolation by reprogramming the local immune environment through local immune suppression.

In this study, fabrication of a polymer scaffold with highly controlled templated construct for the application of supporting seeded cells in cell replacement therapy for diabetes was demonstrated. A highly porous and flexible polymer scaffold matrix was produced and designed specifically for the infiltration and retention of pancreatic islets. This study demonstrated that islets were reliably packed within scaffolds at high packing densities that extend throughout the thickness of the material. Cell viability and functional studies suggested that the material is compatible with cell viability and the key function of glucose stimulated insulin secretion by islets is not negatively impacted by the scaffold. Both stem cell derived beta-cell clusters and primary mouse islets could be packed within a scaffold and transplanted into mouse recipients. Transplanted cells are not only viable but also function as they show efficacy in correcting high glucose in diabetic animal models. Finally, the ability to elute immune suppressive drugs from the matrix with the goal of achieving local immune modulation to prevent graft rejection by the host immune system was illustrated.

FIG. 1 shows the fabrication scheme for polymer-porogen slurry. Polycaprolactone and polyethyelene glycol are dissolved in trifluoroethanol in a 70° C. water bath overnight. Sodium chloride particles were then introduced to the homogenous polymer mixture to yield a super-saturated polymer-porogen slurry. The slurry was agitated to mix thoroughly before casting onto templated silicon PDMS substrate and allowed to dry overnight. Porogen leaching was performed in deionized water for 5 days to fully remove the salt.

FIGS. 5A and 5B show characterization of viability and insulin secretion function in cell and islet loaded scaffolds. FIG. 5A shows fluorescent intensity measured from mCherry expressing Minh cells loaded on tissue culture plastic or PCL scaffold. (n=4 per group). FIG. 5B shows insulin secretion kinetics in response to low (2 mM), high (20 mM), and low (2 mM) glucose perifusion challenge for free islets, and islets seeded on uncoated, collagen coated, and laminin coated PCL scaffolds. (n=3 per group).

Figure 9A:
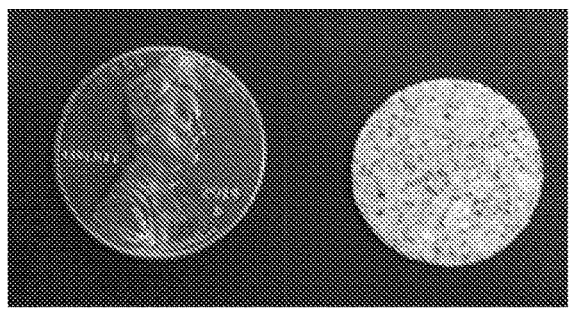
FIGS. 9A-9F are a collection of images showing features of a porous PCL scaffold, according to embodiments of the present disclosure. Scale bar in FIG. 9D is 200 µm and scale bar in FIG. 9E-F is 100 µm.
Figure 9B:
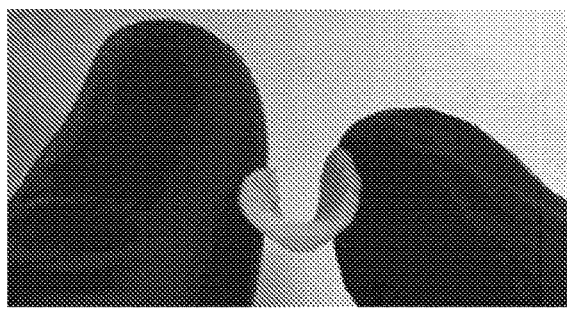
Figure 9C:
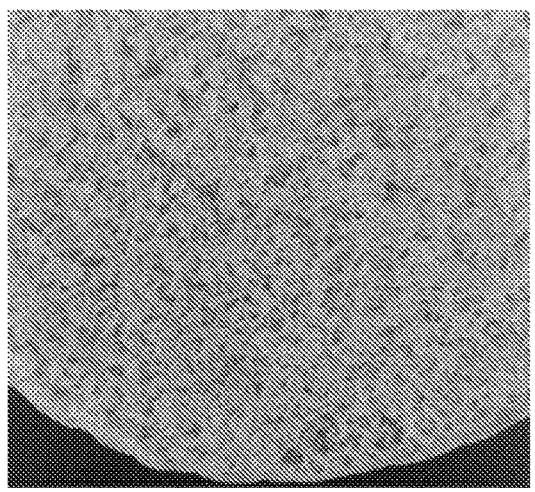
Figure 9D:
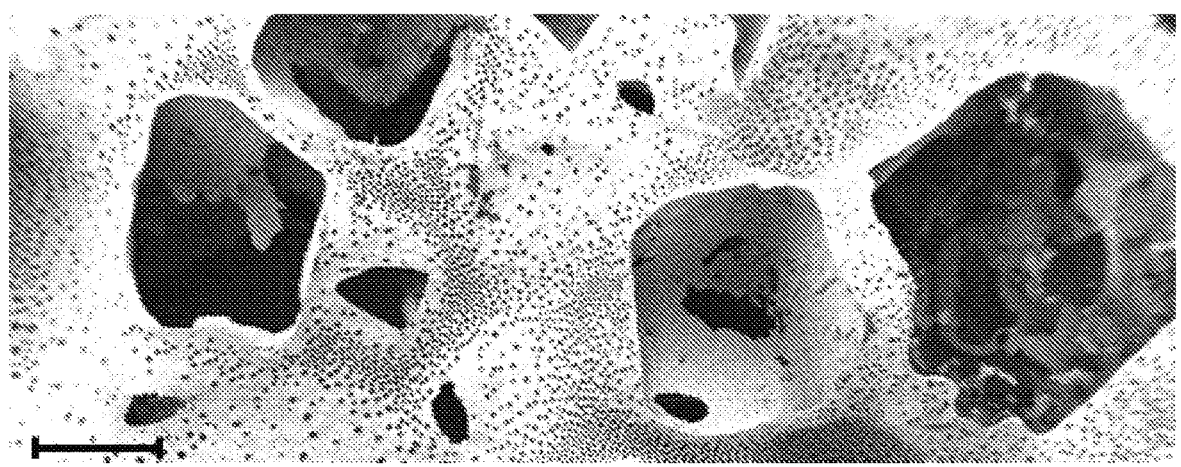
Figure 9E:
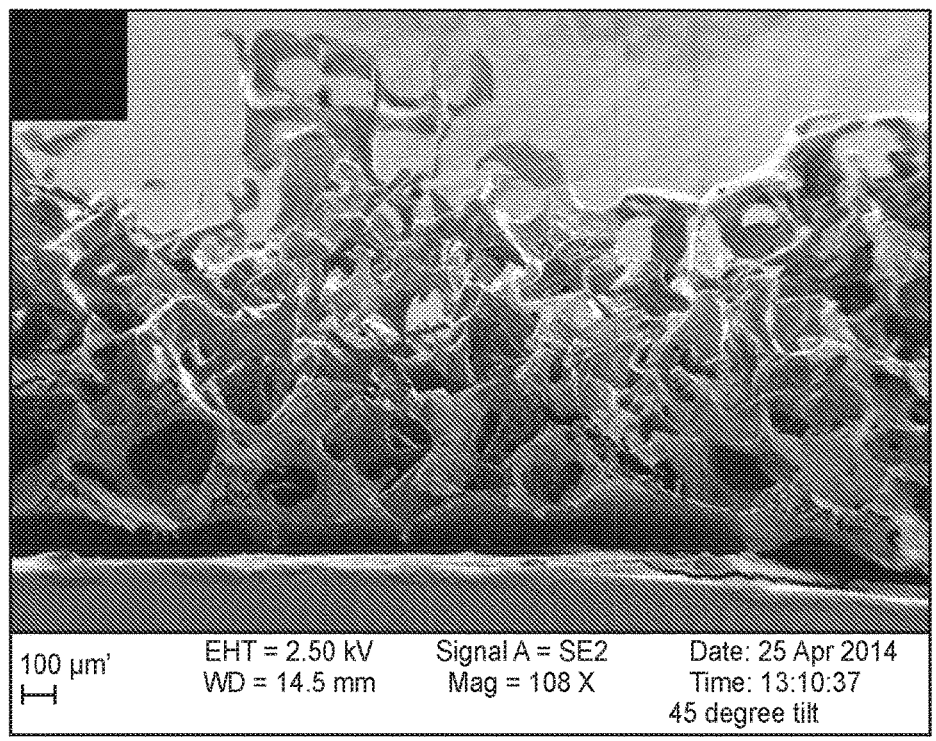
Figure 9F:
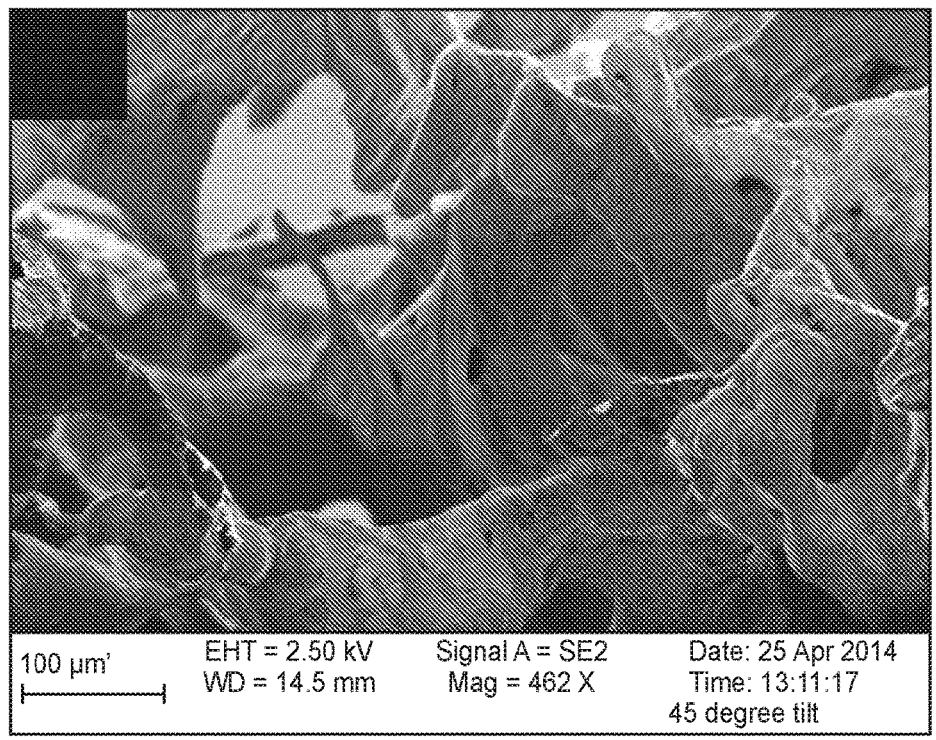

FIGS. 9A-9F show polycaprolactone scaffold for cell seeding. FIG. 9A shows gross image of polymer scaffold cut to a circular wafer. FIG. 9B shows a gross image of polymer scaffold showing flexibility of material. FIG. 9C shows a scaffold image showing highly porous architecture within the matrix. FIG. 9D shows a scanning electron microscopy image of the polymer scaffold. FIG. 9E shows a scanning electron micrograph of pores within the polymer scaffold. FIG. 9E-F shows a scanning electron microscopy image of cross section of polymer scaffold showing thickness and pores within matrix.

FIGS. 10A-10E show in vivo efficacy of stem cell derived beta cell clusters and mature mouse islets seeded on scaffolds. FIG. 10A shows fluorescent microscopy of stem cells transduced with GFP reporter driven off insulin promotor within scaffolds. FIG. 10B shows in vivo luciferase bioluminescent image of stem-cell scaffold construct on day 0 and 30 after subcutaneous transplant into NSG mice. FIG. 10C shows a schematic illustration of differentiation schedule of stem cell derived beta cells and stage at which cells were loaded into scaffolds; and bioluminescent imaging showing loaded stem cells are viable within scaffolds. FIG. 10D shows a bioluminescent image of stem cells transplanted without scaffolds in the subcutaneous space and in the kidney capsule of NSG mice on day 0 and 7 following transplantation; and quantification bioluminescent intensity of subcutaneous and kidney capsule transplants up to day 20. FIG. 10E shows glucose levels of STZ induced diabetic B6 mice that received epidydimal transplants with syngeneic islets with or without scaffolds. (n=3 per group).

FIGS. 11A and 11B show a template fabrication for polymer scaffold. FIG. 11A shows templated acrylic mold consisting of 500 micron wells with 50 micron spacing textured in a honeycomb pattern following laser cutting. FIG. 11B shows templated PDMS negative mold consisting of 500 micron posts with 50 micron spacing textured in honeycomb pattern.

FIGS. 12A-12C shows characterization of scaffold retention of single beta cells and islet clusters. FIG. 12A shows MING cells loaded onto scaffolds measuring 0.36 cm$^2$ in area and 1 mm in thickness at $2.5 \times 10^5$, $5 \times 10^5$, and $10^6$ cells per scaffold. Scaffolds were also coated with either collagen, laminin, or collagen and laminin. Percent retention was measured by fraction of cells retained on scaffold after being transferred into a new well. (n=6 per group). FIG. 12B shows representative fluorescent confocal microscopy of 100 MIP-Luc islet clusters loaded within PCL scaffolds. FIG. 12C shows mean fluorescent intensity (y-axis) as measured throughout the thickness of the entire scaffold (x-axis).

FIGS. 13A-13C shows characterization of loading efficiency and capacity of PCL scaffolds. FIG. 13A shows a brightfield image of PLGA microsphere loaded into PCL scaffolds. FIG. 13B shows a z-stack composite image of fluorescence confocal microscopy of GFP labeled 150 micrometer PLGA microspheres loaded within scaffold, and a plot of intended microsphere count loaded (x-axis) and microsphere count retained on scaffold (y-axis) for scaffolds measuring 1 mm and 1.5 mm in thickness respective. FIG. 13C shows a plot of retention efficiency of scaffolds with each successive attempt to load 50 additional microspheres. (n=4 per group).

FIGS. 14A and 14B show local release of Rapamycin from nonporous PCL ring. FIG. 14A shows Rapamycin mixed within a polymer matrix is released in a controlled and continuous fashion over the course of a month. Plot shows two sets of samples. (n=2 per group). FIG. 14B shows quantification of mass from anti-mouse IgG conjugated onto polycaprolactone surfaces using NHSS-EDC chemistry.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A polycaprolactone (PCL) scaffold consisting of:
a monolithic, continuous structure comprising a plurality of pores, wherein the plurality of pores comprises macropores interconnected by struts containing micropores, wherein the macropores have an average diameter of from 50 μm to 500 μm and the micropores have an average diameter of 20 μm or less; and
wells that are distinct from the plurality of pores and that are arranged on the surface of the scaffold in a honeycomb pattern;
wherein the micropores and macropores are present on external surfaces of the PCL scaffold.

2. The PCL scaffold of claim 1, wherein the average distance between the pores is less than about 10 μm.

3. The PCL scaffold of claim 1, wherein the PCL scaffold has a bulk porosity of from about 50% to about 90% as measured by computed tomography scanning of the PCL scaffold.

4. The PCL scaffold of claim 1, wherein the PCL scaffold has a surface porosity of about 75% or more as measured by segmentation of an image of the PCL scaffold surface.

5. The PCL scaffold of claim 1, wherein the PCL scaffold is substantially flat.

6. The PCL scaffold of claim 5, wherein the PCL scaffold has a thickness of from about 0.1 mm to about 25 mm.

7. The PCL scaffold of claim 5, wherein the PCL scaffold has a lateral dimension of from about 1.0 cm to about 10 cm.

8. The PCL scaffold of claim 5, wherein the scaffold is pliable and readily bends under constant stress.

9. The PCL scaffold of claim 1, wherein the PCL scaffold is composed of a single material, wherein the single material is PCL.

10. The PCL scaffold of claim 1, wherein the average diameter of the wells is 500 microns.

11. The PCL scaffold of claim 1, wherein inter-well spacing is the distance between adjacent wells on the surface of the scaffold, and wherein each inter-well spacing varies by 20% or less from the average inter-well spacing.

12. A therapeutic scaffold comprising the PCL scaffold of claim 1 and a plurality of therapeutic cells encapsulated within the macropores of the PCL scaffold.

13. The PCL therapeutic scaffold of claim 12, wherein the plurality of therapeutic cells comprises at least $10^5$ cells.

14. The therapeutic scaffold of claim 12, wherein the therapeutic cells comprise in vitro differentiated stem cells, insulin-secreting cells, human stem cell-derived insulin producing cells (SCIPCs), or lymphocytes.

15. The PCL scaffold of claim 13, wherein the macropores comprise a diameter of 100-300 mm and the micropores comprise a diameter of 5-20 mm.

* * * * *

UNITED STATES PATENT AND TRADEMARK OFFICE
CERTIFICATE OF CORRECTION

PATENT NO. : 12,421,369 B2
APPLICATION NO. : 16/309081
DATED : September 23, 2025
INVENTOR(S) : Tejal A. Desai et al.

It is certified that error appears in the above-identified patent and that said Letters Patent is hereby corrected as shown below:

On the Title Page

Item (57), in Column 2, under "Abstract", Line 2, delete "micorpores" and insert -- micropores --.

In the Drawings

On Sheet 7 of 17, in Figure 8, Line 1 (Y-axis), delete "Sectretion" and insert -- Secretion --.

On Sheet 7 of 17, in Figure 8, Line 1 (X-axis), delete "Conentration" and insert -- Concentration --.

In the Specification

In Column 1, Line 25, delete "micorpores" and insert -- micropores --.

In Column 2, Line 24, delete "ding" and insert -- according --.

In Column 14, Lines 12-27, delete "In some cases, the insulin-secreting cells are primary β islet cells (e.g., mature β islet cells isolated from a pancreas). In some cases, the insulin-secreting cells are β cells, or β-like cells that are derived in vitro from immature cell, precursor cells, progenitor cells, or stem cells. The insulin-secreting cells may be derived from (i.e., obtained by differentiating) stem and/or progenitor cells such as hepatocytes (e.g., transdifferentiated hepatocytes), acinar cells, pancreatic duct cells, stem cells, embryonic stem cells (ES), partially differentiated stem cells, non-pluripotent stem cells, pluripotent stem cells, induced pluripotent stem cells (iPS cells), etc. Suitable insulin-secreting cells and methods of generating the same are described in, e.g., US20030082810; US20120141436; and Raikwar et al. (PLoS One. 2015 Jan. 28; 10(1):e0116582), each of which are incorporated herein by reference." and insert the same on Column 14, Line 11, as a continuation of the same paragraph.

Signed and Sealed this
Sixteenth Day of December, 2025

John A. Squires
*Director of the United States Patent and Trademark Office*

CERTIFICATE OF CORRECTION (continued)
U.S. Pat. No. 12,421,369 B2

In Column 14, Lines 60-65, delete "In some cases, the active agent is an inhibitor of mammalian target of rapamycin (mTOR), such as, without limitation, rapamycin and analogs thereof (e.g., sirolimus, temsirolimus, everolimus, deforolimus, etc.). The mTOR inhibitor may be used as an immunosuppressant, or may be an anticancer agent." and insert the same on Column 14, Line 59, as a continuation of the same paragraph.

In Column 15, Line 14, delete "cefipime," and insert -- cefepime, --.

In Column 15, Line 16, delete "proxctil," and insert -- proxetil, --.

In Column 15, Line 43, delete "aliteretinoin, altertamine," and insert -- alitretinoin, altretamine, --.

In Column 15, Line 44, delete "bicalutarnide," and insert -- bicalutamide, --.

In Column 15, Line 58, delete "cystineamine" and insert -- cysteamine --.

In Column 20, Line 22, delete "of" and insert -- or --.

In Column 20, Line 31, delete "(such" and insert -- such --.

In Column 25, Lines 43-49, delete "Laser Cutter system at the UCSF Center for Advanced Technology to produced etched patterns in acrylic slabs measuring. The acrylic mold is approximately 4×2 inches with honeycomb pattern of 500 micrometer wells neatly patterned across the surface. The final acrylic slab was cleaned by sonicating in a beaker filled with deionized water and isopropryl alcohol (10% v/v)." and insert the same on Column 25, Line 42, as a continuation of the same paragraph.

In Column 26, Line 57, delete "MING" and insert -- MIN6 --.

In Column 27, Line 36, delete "epidydimal" and insert -- epididymal --.

In Column 27, Line 38, delete "epidydimal" and insert -- epididymal --.

In Column 29, Line 40, delete "epidydimal" and insert -- epididymal --.

In Column 30, Line 30, delete "polyethyelene" and insert -- polyethylene --.

In Column 30, Line 42, delete "Minh" and insert -- Min6 --.

In Column 31, Line 9, delete "epidydimal" and insert -- epididymal --.

In the Claims

In Column 32, Line 51, in Claim 13, before "therapeutic" delete "PCL".

In Column 32, Line 58, in Claim 15, delete "mm" and insert -- μm --.

In Column 32, Line 59, in Claim 15, delete "mm." and insert -- μm. --.